(12) United States Patent
Willingham et al.

(10) Patent No.: US 9,623,079 B2
(45) Date of Patent: Apr. 18, 2017

(54) METHODS FOR ACHIEVING THERAPEUTICALLY EFFECTIVE DOSES OF ANTI-CD47 AGENTS FOR TREATING CANCER

(71) Applicant: The Board of Trustees of the Leland Stanford Junior University, Stanford, CA (US)

(72) Inventors: Stephen Willingham, Stanford, CA (US); Maureen Howard, Los Altos Hills, CA (US); Jie Liu, Palo Alto, CA (US); Ravindra Majeti, Palo Alto, CA (US); Susan Sweeney Prohaska, Mountain View, CA (US); Anne Kathrin Volkmer, Duesseldorf (DE); Jens-Peter Volkmer, Menlo Park, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 15 days.

(21) Appl. No.: 14/769,069

(22) PCT Filed: Feb. 26, 2014

(86) PCT No.: PCT/US2014/018743
§ 371 (c)(1),
(2) Date: Aug. 19, 2015

(87) PCT Pub. No.: WO2014/149477
PCT Pub. Date: Sep. 25, 2014

(65) Prior Publication Data
US 2016/0008429 A1 Jan. 14, 2016

Related U.S. Application Data

(60) Provisional application No. 61/800,102, filed on Mar. 15, 2013.

(51) Int. Cl.
*A61K 39/395* (2006.01)
*A61K 38/16* (2006.01)
(Continued)

(52) U.S. Cl.
CPC ...... *A61K 38/1816* (2013.01); *A61K 39/3955* (2013.01); *C07K 16/2803* (2013.01);
(Continued)

(58) Field of Classification Search
None
See application file for complete search history.

(56) References Cited

U.S. PATENT DOCUMENTS 9,151,760 B2 * 10/2015 Weissman .......... G01N 33/5743
9,352,037 B2    5/2016 van den Berg
(Continued)

FOREIGN PATENT DOCUMENTS

WO    2009091547 A1    7/2009
WO    2009091601 A1    7/2009
(Continued)

OTHER PUBLICATIONS

Kim et al., Anti-CD47 antibodies promote phagocytosis and inhibit the growth of human myeloma cells. Leukemia. 26(12):2538-45, Dec. 2012, Epub May 30, 2012.*
(Continued)

*Primary Examiner* — Claire Kaufman
(74) *Attorney, Agent, or Firm* — Pamela J. Sherwood; Kyle A. Gurley; Bozicevic, Field & Francis LLP

(57) ABSTRACT

Methods are provided for treating a subject with a therapeutic dose of anti-CD47 agent by administering a primer agent prior to administering a therapeutically effective dose of an anti-CD47 agent to the subject.

12 Claims, 14 Drawing Sheets
(8 of 14 Drawing Sheet(s) Filed in Color)

(51) Int. Cl.
  A61K 38/18   (2006.01)
  C07K 16/28   (2006.01)
  A61K 39/00   (2006.01)
(52) U.S. Cl.
  CPC .... *C07K 16/2896* (2013.01); *A61K 2039/505* (2013.01); *A61K 2039/54* (2013.01); *A61K 2039/545* (2013.01); *C07K 2317/24* (2013.01); *C07K 2317/33* (2013.01); *C07K 2317/73* (2013.01); *C07K 2317/76* (2013.01); *C07K 2317/92* (2013.01); *C07K 2319/30* (2013.01)

(56) References Cited

U.S. PATENT DOCUMENTS

| | | |
|---|---|---|
| 2004/0213792 A1 | 10/2004 | Clemmons et al. |
| 2007/0113297 A1 | 5/2007 | Yang et al. |
| 2010/0239578 A1 | 9/2010 | Danska et al. |
| 2010/0323949 A1 | 12/2010 | Lu et al. |
| 2012/0282174 A1 | 11/2012 | Weissman et al. |
| 2014/0140989 A1 | 5/2014 | Eckelman et al. |

FOREIGN PATENT DOCUMENTS

| | | |
|---|---|---|
| WO | 2011143624 | 11/2011 |
| WO | 2013109752 | 7/2013 |

OTHER PUBLICATIONS

Majeti et al., CD47 is an adverse pronostic factor and therapeutic antibody target on human acute myeloid leukemia stem cells, Cell, 138:286-299, Jul. 2009.*
Willingham et al., The CD47-signal regulatory protein alpha (SIRPa) interaction is a therapeutic target for human solid tumors, Proc. Natl. Acad. Sci. USA, 109(17):6662-6667, Apr. 24, 2012, Epub Mar. 26, 2012.*
Chao et al., Anti-CD47 antibody synergizes with rituximab to promote phagocytosis and eradicate Non-Hodgkin Lymphoma, Cell, 142:699-713, Sep. 3, 2010.*
Alinari et al.,"Alemtuzumab (Campath-1H) in the treatment of chronic lymphocytic leukemia", Oncogene, 2007, pp. 3644-3653, 26, Nature Publishing Group, London, United Kingdom.
Burger et al., "Phase II Trial of Bevacizumab in Persistent or Recurrent Epithelial Ovarian Cancer or Primary Peritoneal Cancer: A Gynecologic Oncology Group Study", Journal of Clinical Oncology, Nov. 20, 2007, pp. 5165-5172, vol. 25, No. 33, American Society of Clinical Oncology, Alexandria, VA.
Clynes et al., "Inhibitory Fc receptors modulate in vivo cytoxicity against tumor targets", Nature Medicine, Apr. 2000, pp. 443-446, vol. 6, No. 4, Nature Publishing Group, London, United Kingdom.
Curriculum Vitae Randolph Wall, Ph.D., 9 pages.
Declaration of Randolph Wall, Ph.D., 107 Pages.
Imai et al., "Comparing antibody and small-molecule therapies for cancer", Nature Reviews/Cancer, Sep. 2006, pp. 714-727, vol. 6, Nature Publishing Group, London, United Kingdom.
Kim et al., "Antibody Engineering for the Development of Therapeutic Antibodies", Molecules and Cells, Aug. 18, 2005, pp. 17-29, vol. 20, No. 1, Korean Society for Molecular and Cellular Biology, Seoul, Korea.
Mawby et al., "Isolation and characterization of CD47 glycoprotein: a multispanning membrane protein which is the same as integrin-associated protein (IAP) and the ovarian tumour marker OA3", Biochem. J., 1994, pp. 525-530, 304, Portland Press Limited, London, United Kingdom.
Musolino et al., Immunoglobulin G Fragment C Receptor Polymorphisms and Clinical Efficacy of Trastuzumab-Based Therapy in Patients With HER-2/neu-Positive Metastatic Breast Cancer, Journal of Clinical Oncology, Apr. 10, 2008, pp. 1789-1796, vol. 26, No. 11, American Society of Clinical Oncology, Alexandria, VA.
Okazawa et al., "Negative Regulation of Phagocytosis in Macrophages by the CD47-SHPS-1 System", The Journal of Immunology, 2005, pp. 2004-2011, 174, The American Association of Immunologists, Inc., Bethesda, MD.
Ozols, "Challenges for chemotherapy in ovarian cancer", Annals of Oncology, May 2006, pp. v181-v187, vol. 17, Supplement 5, European Society for Medical Oncology, Lugano, Switzerland.
Forty Seven, Inc., Petition for Inter Partes Review of U.S. Pat. No. 9,352,037, Filed: Aug. 5, 2016, Case No. PR2016-01529, 74 Pages.
Forty Seven, Inc., Petition for Inter Partes Review of U.S. Pat. No. 9,352,037, Filed: Aug. 8, 2016, Case No. PR2016-01530, 76 Pages.
Tibes et al., "Activity of Alemtuzumab in Patients with CD52-Positive Acute Leukemia", Cancer, Jun. 15, 2006, pp. 2645-2651, vol. 106, No. 12, American Cancer Society, Atlanta, GA.
Veillette et al., "High Expression of Inhibitory Receptor SHPS-1 and Its Association with Protein-tyrosine Phosphatase SHP-1 in Macrophages", The Journal of Biological Chemistry, Aug. 28, 1998, pp. 22719-22728, vol. 273, No. 35, The American Society for Biochemistry and Molecular Biology, Inc., Rockville, MD.
Zheng et al., "Gene expression profiling of CD34b cells identifies a molecular signature of chronic myeloid leukemia Blast crisis", Leukemia, Apr. 13, 2006, pp. 1028-1034, 20, Nature Publishing Group, London, United Kingdom.
Oldenborg et al., CD47-Signal Regulatory Protein α (Sirpα) Regulates Fcγ and Complement Receptor-Mediated Phagocytosis, The Journal of Experimental Medicine, Apr. 2, 2001 (Apr. 2, 2001 ), vol. 193, No. 7, pp. 855-862.
Szenajch et al., "The role of erythropoietin and its receptor in growth, survival and therapeutic response of human tumor cells", BBA—Reviews on Cancer, Aug. 1, 2010, pp. 82-95, vol. 1806, No. 1, Elsevier Science, Amsterdam, Netherlands.

* cited by examiner

Fig. 4

```
                        10         20         30         40         50         60
Human CD47ECD   QLLFNKTKSVEFTFCNDTVVIPCFVTNMEAQNTTEVYVKWKFKGRDIYTFDGALNKSTVP
                ::::::::::::::::::::::::::::::::::::::::::::::::::::::::::::
Cyno  CD47ECD   QLLFNKTKSVEFTFCNDTVVIPCFVTNMEAQNTTEVYVKWKFKGRDIYTFDGALNKSTAP
                        10         20         30         40         50         60

70         80         90        100        110        120
Human CD47ECD   TDFSSAKIEVSQLLKGDASLKMDKSDAVSHTGNYTCEVTELTREGETIIELKYRVVSWFS
                ..::::::::::::::::::::::::::::::::::::::::::::::::::::::::::
Cyno  CD47ECD   ANFSSAKIEVSQLLKGDASLKMDKSDAVSHTGNYTCEVTELTREGETIIELKYRVVSWFS
                        70         80         90        100        110        120

Human CD47ECD   PNEN
                ::::
Cyno  CD47ECD   PNEN
```

| Fig. 6A | ka (M⁻¹s⁻¹) | kd (s⁻¹) | KD (pM) |
|---|---|---|---|
| assay 1 | 5.13E5 | 7.34E-6 | 14.3 |
| assay 2 | 4.94E5 | 1.00E-6 | 2.02 |
| Average | 5.0(1)E5 | 4(4)E-6 | 8(8) |

| Fig. 6B | ka (M⁻¹s⁻¹) | kd (s⁻¹) | KD (pM) |
|---|---|---|---|
| assay 1 | 2.27E5 | 2.75E-6 | 12.1 |
| assay 2 | 2.76E5 | 2.00E-6 | 7.239 |
| Average | 2.5(3)E5 | 2.4(5)E-6 | 10(3) |

Fig. 11A
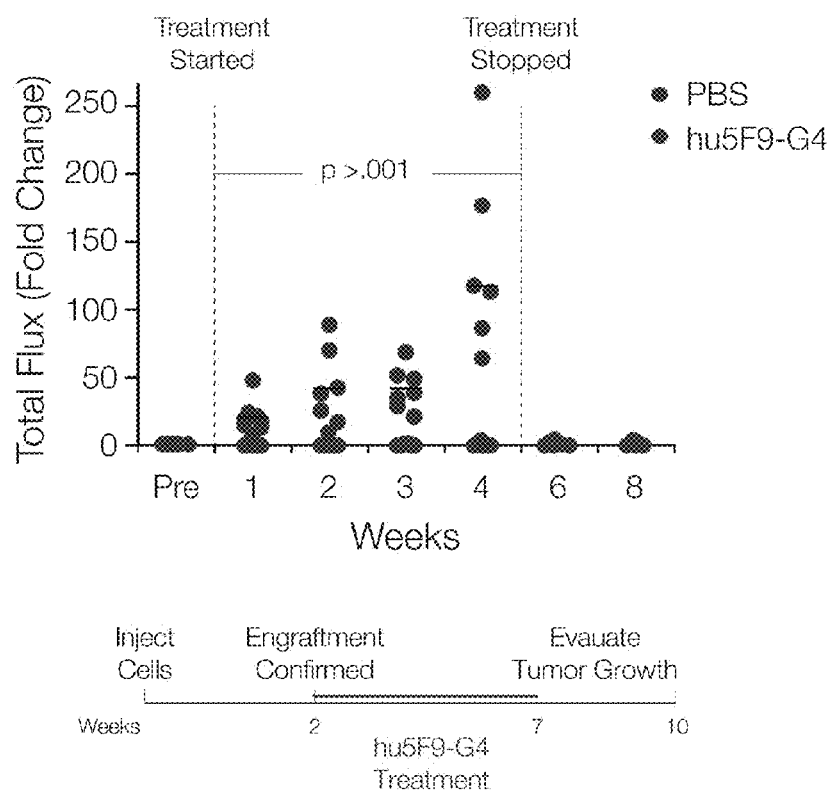
Fig. 11B
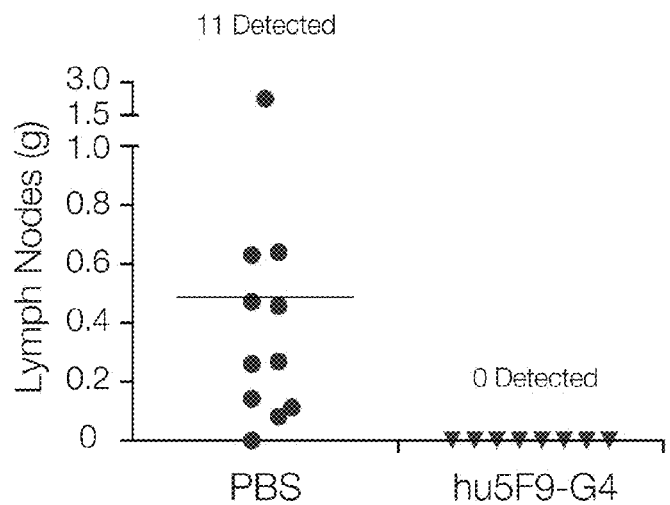
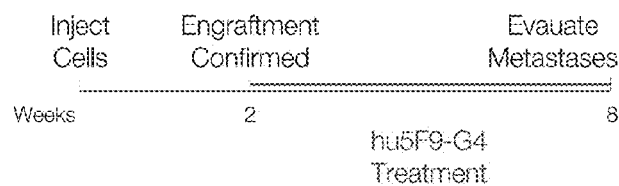

Fig. 13

STUDY DESIGN

| Group | Priming Dose | Maintenance Dose | Number (Males/Females) |
|---|---|---|---|
| 1 | 0 (Vehicle) | 0 (Vehicle) | 5/5 |
| 2 | 5 mg/kg | 10 mg/kg | 3/3 |
| 3 | 5 mg/kg | 50 mg/kg | 5/5 |
| 4 | 5 mg/kg | 100 mg/kg | 5/5 |
| 5 | 5 mg/kg | 5 mg/kg | 2/2 |

[A] The priming dose was administered on Day 1

[B] Maintenance dose was administered twice weekly on Days 8, 11, 15, 18, 22, 25, 29, 32, 36, 39, 43, 46, 50, and 53.

[C] Final "Maintenance dose" administered at Day 53, but animals were monitored till Day 95

SEQUENCE LISTING

<160> NUMBER OF SEQ ID NOS: 5

<210> SEQ ID NO 1
<211> LENGTH: 124
<212> TYPE: PRT

<213> ORGANISM: Homo sapiens

<400> SEQUENCE: 1

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn
        115                 120

<210> SEQ ID NO 2
<211> LENGTH: 18
<212> TYPE: PRT
<213> ORGANISM: Artificial Sequence
<220> FEATURE:
<223> OTHER INFORMATION: Sythetic polypeptide sequence

<400> SEQUENCE: 2

Met Trp Pro Leu Val Ala Ala Leu Leu Leu Gly Ser Ala Cys Cys Gly
1               5                   10                  15

Ser Ala

<210> SEQ ID NO 3
<211> LENGTH: 142
<212> TYPE: PRT
<213> ORGANISM: Homo sapiens

<400> SEQUENCE: 3

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn
    130                 135                 140

```
<210> SEQ ID NO 4
<211> LENGTH: 124
<212> TYPE: PRT
<213> ORGANISM: Homo sapiens

<400> SEQUENCE: 4

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn
            115                 120

<210> SEQ ID NO 5
<211> LENGTH: 124
<212> TYPE: PRT
<213> ORGANISM: Macaca mulatta

<400> SEQUENCE: 5

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Ala Pro Ala Asn Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn
            115                 120
```

METHODS FOR ACHIEVING THERAPEUTICALLY EFFECTIVE DOSES OF ANTI-CD47 AGENTS FOR TREATING CANCER

BACKGROUND

Turnover of cells begins with the induction of an apoptotic program or other cellular changes that mark them for removal, and the subsequent recognition of markers by phagocytes, including macrophages, dendritic cells, and the like. This process requires a specific and selective removal of unwanted cells. Unlike healthy cells, the unwanted/aged/dying cells display markers or ligands called "eat-me" signals, i.e. "altered self", which can in turn be recognized by receptors on the phagocytes. Healthy cells may display "don't eat-me" signals that actively inhibit phagocytosis; these signals are either downregulated in the dying cells, are present in an altered conformation or they are superseded by the upregulation of "eat-me" or pro-phagocytic signals. The cell surface protein CD47 on healthy cells and its engagement of a phagocyte receptor, SIRPα, constitutes a key "don't eat-me" signal that can turn off engulfment mediated by multiple modalities, including apoptotic cell clearance and FcR mediated phagocytosis. Blocking the CD47 mediated engagement of SIRPα on a phagocyte, or the loss of CD47 expression in knockout mice, can cause removal of live cells and non-aged erythrocytes. Blocking SIRPα also allows engulfment of targets that are not normally phagocytosed, for those cells where pre-phagocytic signals are also present.

CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2007) J.B.C. 282:14567-75; and the role of SIRPα cis dimerization in CD47 binding is discussed by Lee et al. (2010) J.B.C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

Programmed cell death (PCD) and phagocytic cell removal are common ways that an organism responds in order to remove damaged, precancerous, or infected cells. Thus, the cells that survive this organismal response (e.g., cancerous cells, chronically infected cells, etc.) have devised ways to evade PCD and phagocytic cell removal. CD47, the "don't eat me" signal, is constitutively upregulated on a wide variety of diseased cells, cancer cells, and infected cells, allowing these cells to evade phagocytosis. Anti-CD47 agents that block the interaction between CD47 on one cell (e.g., a cancer cell, an infected cell, etc.) and SIRPα on another cell (e.g., a phagocytic cell) counteract the increase of CD47 expression and facilitate the phagocytosis of the cancer cell and/or the infected cell. Thus, anti-CD47 agents can be used to treat and/or protect against a wide variety of conditions/disorders.

However, an initial high dose of an anti-CD47 agent can cause a dose-dependent loss of red blood cells (RBCs) in mice and non-human primate (NHP) models. The severity of this anemia can preclude the use of higher doses that are required to achieve sustained serum concentrations associated with therapeutic efficacy. The present invention provides methods by which the erythrocyte toxicity of anti-CD47 agents is mitigated, thereby enabling treatment with therapeutically effective amounts of anti-CD47 agents.

SUMMARY OF THE INVENTION

Methods are provided for treating an individual with a therapeutic dose of anti-CD47 agent by administering a primer agent prior to administering a therapeutically effective dose of an anti-CD47 agent to the individual. In some embodiments, the methods of the invention find use in optimizing therapies aimed at modulating CD47-mediated phagocytosis. In some such embodiments, the individual is being treated with a dose of anti-CD47 agent for cancer. In other embodiments the individual is being treated with a dose of anti-CD47 agent for infection with an intracellular pathogen. In the subject methods, a therapeutically effective dose of an anti-CD47 agent is administered from about 3 days to about 21 days after administering a primer agent.

In some embodiments of the invention, two or more primer agents are administered. Suitable primer agents include an erythropoiesis-stimulating agent (ESA), and/or a priming dose of an anti-CD47 agent.

An anti-CD47 agent for use in the methods of the invention interferes with binding between CD47 present on a target cell, including without limitation a cancer cell, a cell infected with an intracellular pathogen, a stem cell, etc., to SIRPα present on a phagocytic cell. Generally both such cells are present in the individual being treated. Such methods, in the presence of a pro-phagocytic signal, can increase phagocytosis of the target cell. The subject methods can be used to treat a subject for any disease susceptible to blockade of CD47-mediated SIRPα signaling. Suitable anti-CD47 agents include soluble SIRPα polypeptides; soluble CD47; anti-CD47 antibodies, anti-SIRPα antibodies, and the like, where the term antibodies encompasses antibody fragments and variants thereof, as known in the art.

Therapeutic doses of anti-CD47 agents as described above can lead to a loss of erythrocytes (RBCs) and anemia. The methods of the invention address this problem, and surprisingly show that a primer agent, as used herein, significantly reduces toxicity due to loss of erythrocytes. Without being bound by theory, it is believed that the primer agent increases production of reticulocytes (immature RBC), which may be more resistant to CD47 mediated phagocytosis and therefore are less susceptible to loss during subsequent administration of the anti-CD47 agent.

Certain embodiments of the invention optionally include a step of determining responsiveness of an individual to administration of the primer agent. For example, a reticulocyte count, or a decrease in hemoglobin, can be used to determine whether administration of the primer agent increased production of reticulocytes. A reticulocyte count can be performed prior to and following primer agent administration, allowing for a period of time between counts that is effective for an increase in reticulocytes. Alternatively, any suitable methods for determination of increased erythropoiesis can be used.

Following administration of the priming agent, and allowing a period of time effective for an increase in reticulocyte production, a therapeutic dose of an anti-CD47 agent is administered. The therapeutic dose can be administered in number of different ways. In some embodiments, two or more therapeutically effective doses are administered after a primer agent is administered. In some embodiments a therapeutically effective dose of an anti-CD47 agent is administered as two or more doses of escalating concentration, in others the doses are equivalent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 depicts a sequence alignment between human and macaque CD47 in the Ig-like extracellular domain. Human CD47ECD (SEQ ID NO: 4); Cyno (macaque) CD47ECD (SEQ ID NO: 5).

FIG. 6A-6B presents a summary of binding constants measured for Hu5F9-G4 binding. SPR binding studies were performed on a BioRad ProteOn XPR36 system using a GLM sensor chip. Binding data were collected at 25° C. Response data were globally fit using a 1:1 interaction model. The number in parentheses represents the standard error in the last reported digit. (FIG. 6A) Binding to human CD47. (FIG. 6B) Binding to cynomolgus CD47.

(FIG. 7A) Anemia developed in a dose-dependent manner, but resolved spontaneously. The shaded bar indicates the range of hemoglobin that indicates the need for transfusion in humans. (FIG. 7B) Pharmacokinetic (PK) analysis by measurement of serum levels indicated a short-half life with therapeutic levels achieved by 10 and 30 mg/kg, but not the other doses.

(FIG. 8A) Hemoglobin was serially measured to monitor anemia. (FIG. 8B) Serum was screened for the level of Hu5F9-G4 by ELISA to determine pharmacokinetics (PK). In panel (FIG. 8A), the shaded bar indicates the range of hemoglobin in humans that tends to trigger transfusion. In panel (FIG. 8B), the shaded bar indicates the range of serum Hu5F9-G4 associated with potent efficacy in xenograft studies.

(FIG. 9A) Hemoglobin was serially measured to monitor anemia. (FIG. 9B) Serum was screened for the level of Hu5F9-G4 by ELISA to determine pharmacokinetics. In panel (FIG. 9A), the shaded bar indicates the range of hemoglobin in humans that might trigger transfusion. In panel (FIG. 9B), the shaded bar indicates the range of serum Hu5F9-G4 associated with potent efficacy against primary human AML in xenograft studies (i.e., the range of therapeutically effective serum levels).

FIG. 11A-11B demonstrates that Hu5F9-G4 inhibits tumor growth and metastasis. FIG. 11A) Hu5F9-G4 fully eliminates bladder cancer in xenotransplantation assays. FIG. 11B) Hu5F9-G4 prevents human prostate cancer metastasis in vivo.

FIG. 12A-12B) Hu5F9-G4 eliminates metastatic breast cancer cells in the lungs (FIG. 12A) and brain (FIG. 12B). FIG. 12C) Hu5F9-G4 inhibits regrowth of resected breast tumors. FIG. 12D) Serum concentrations of hu5F9-G4 associated with therapeutic efficacy. Thus, humanized antibodies (e.g., hu5F9-G4), have the same general properties related to the treatment of disease (e.g., cancer or chronic infection) as the non-humanized antibodies and the subject methods will be effective when using a humanized antibody (e.g., anti-CD47 antibody) to treat cancer and/or to treat chronic infection.

FIG. 13 depicts the study design described in Example 4.

DETAILED DESCRIPTION

Figure 1A:
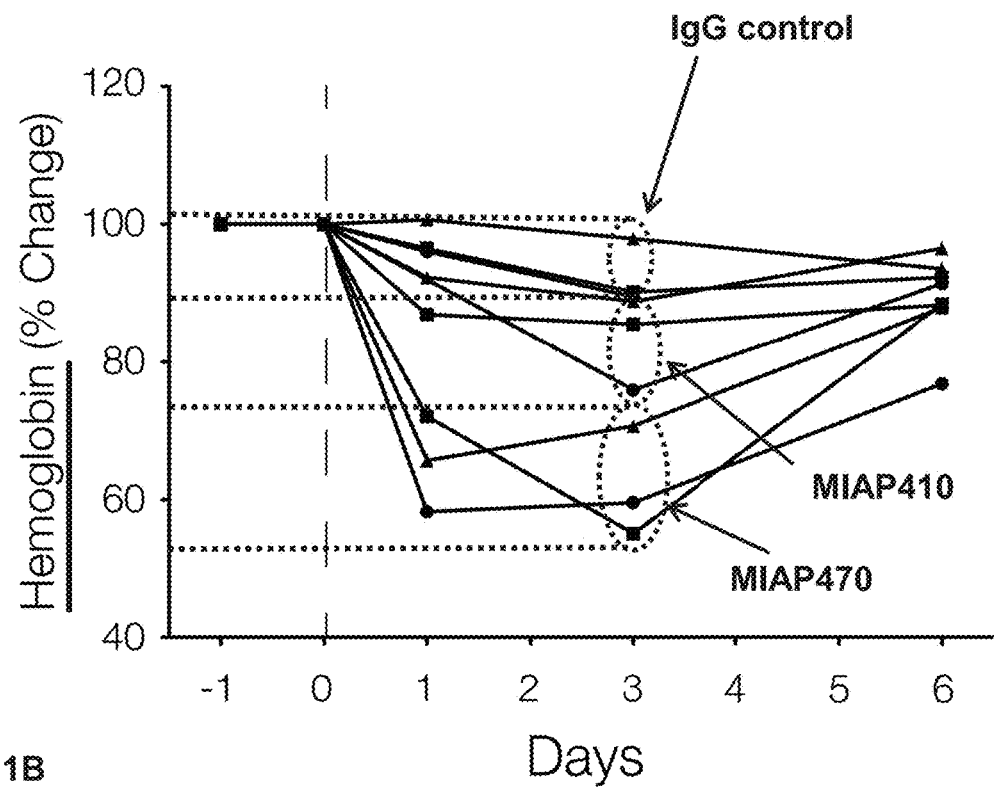
FIG. 1A-1B presents percent change in hematocrit (HCT) and percent change hemoglobin after a single 250 µg IP injection of MIAP410 (IgG1 isotype) or MIAP470 (IgG2a isotype) was administered to wild type mice.

The present invention relates to methods of treating a subject with a therapeutic dose of anti-CD47 agent by first administering a primer agent.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Anti-CD47 agent. As used herein, the term "anti-CD47 agent" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα. In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent (further described below). In an exemplary assay, target cells are incubated in the presence or absence of the candidate agent. An agent for use in the methods of the invention will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 180%, or at least 200%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1, 2004). Thus, in some embodiments, the anti-CD47 agent does not directly induce cell death of a CD47-expressing cell.

Some pathogens (e.g., pox viruses, Myxoma virus, Deerpox virus, swinepox virus, goatpox virus, sheeppox virus, etc.) express a CD47-analog (i.e., a CD47 mimic) (e.g., the M128L protein) that acts as a virulence factor to enable infection (Cameron et al., Virology. 2005 Jun. 20; 337(1): 55-67), and some pathogens induce the expression of endogenous CD47 in the host cell. Cells infected with a pathogen that expresses a CD47-analog may therefore express the pathogen-provided CD47 analog either exclusively or in combination with endogenous CD47. This mechanism allows the pathogen to increase CD47 expression (via expression of the CD47 analog) in the infected cell with or without increasing the level of endogenous CD47. In some embodiments, an anti-CD47 agent (e.g., anti-CD47 antibody, a SIRPα reagent, a SIRPα antibody, a soluble CD47 polypeptide, etc.) can reduce the binding of a CD47 analog (i.e., a CD47 mimic) to SIRPα. In some cases, a suitable anti-CD47 agent (e.g., a SIRPα reagent, an anti-CD47 antibody, etc.) can bind a CD47 analog (i.e., a CD47 mimic) to reduce the binding of the CD47 analog to SIRPα. In some cases, a suitable anti-CD47 agent (e.g., an anti-SIRPα antibody, a soluble CD47 polypeptide, etc.) can bind to SIRPα. A suitable anti-CD47 agent that binds SIRPα does not activate SIRPα (e.g., in the SIRPα-expressing phagocytic cell). An anti-CD47 agent can be used in any of the methods provided herein when the pathogen is a pathogen that provides a CD47 analog. In other words the term "CD47," as used herein, encompasses CD47 as well as CD47 analogs (i.e., CD47 mimics).

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα. In some embodiments, a SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide (SEQ ID NO:2), such that the extracellular portion of CD47 is typically 142 amino acids in length, and has the amino acid sequence set forth in SEQ ID NO:3. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. In an exemplary embodiment, the CD47 extracellular domain lacking the signal peptide has the amino acid sequence set forth in SEQ ID NO:1 (124 amino acids). As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to SEQ ID NO:1.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.).

A target cell may be a cell that is "inflicted", where the term "inflicted" is used herein to refer to a subject with symptoms, an illness, or a disease that can be treated with an anti-CD47 agent. An "inflicted" subject can have cancer, can harbor an infection (e.g., a chronic infection), and other hyper-proliferative conditions, for example sclerosis, fibrosis, and the like, etc. "Inflicted cells" may be those cells that cause the symptoms, illness, or disease. As non-limiting examples, the inflicted cells of an inflicted patient can be cancer cells, infected cells, and the like. One indication that an illness or disease can be treated with an anti-CD47 agent is that the involved cells (i.e., the inflicted cells, e.g., the cancerous cells, the infected cells, etc.) express an increased level of CD47 compared to normal cells of the same cell type.

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

Examples of symptoms, illnesses, and/or diseases that can be treated with an anti-CD47 agent include, but are not limited to cancer and infection (e.g., chronic infection). As used herein "cancer" includes any form of cancer (e.g., leukemia; acute myeloid leukemia (AML); acute lymphoblastic leukemia (ALL); metastasis; minimal residual disease; solid tumor cancers, e.g., breast, bladder, colon, ovarian, glioblastoma, leiomyosarcoma, and head & neck squamous cell carcinomas; etc.). Any cancer, where the cancer cells exhibit increased expression of CD47 compared to non-cancer cells, is a suitable cancer to be treated by the subject methods and compositions.

As used herein, the term "infection" refers to any state in at least one cell of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) that induces increased CD47 expression in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium*, *Chlamydophila*, *Ehrlichia*, *Rickettsia*, *Brucella*, *Legionella*, *Francisella*, *Listeria*, *Coxiella*, *Neisseria*, *Salmonella*, *Yersinia* sp, *Helicobacter pylori* etc.; and intracellular protozoan pathogens, e.g. *Plasmodium* sp, *Trypanosoma* sp., *Giardia* sp., *Toxoplasma* sp., *Leishmania* sp., etc.

As used herein, a "target cell" is a cell expressing CD47 on the surface, where masking or otherwise altering the CD47 positive phenotype (e.g., by administration of an anti-CD47 agent) results in increased phagocytosis. Usually a target cell is a mammalian cell, for example a human cell.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

A "therapeutically effective dose" or "therapeutic dose" is an amount sufficient to effect desired clinical results (i.e., achieve therapeutic efficacy). A therapeutically effective dose can be administered in one or more administrations. For purposes of this invention, a therapeutically effective dose of an anti-CD47 agent is an amount that is sufficient to palliate, ameliorate, stabilize, reverse, prevent, slow or delay the progression of the disease state (e.g., cancer or chronic infection) by increasing phagocytosis of a target cell (e.g., a target cell). Thus, a therapeutically effective dose of an anti-CD47 agent reduces the binding of CD47 on an target cell, to SIRPα on a phagocytic cell, at an effective dose for increasing the phagocytosis of the target cell.

In some embodiments, a therapeutically effective dose leads to sustained serum levels of anti-CD47 agent (e.g., an anti-CD47 antibody) of about 40 μg/ml or more (e.g., about 50 ug/ml or more, about 60 ug/ml or more, about 75 ug/ml or more, about 100 ug/ml or more, about 125 ug/ml or more, or about 150 ug/ml or more). In some embodiments, a therapeutically effective dose leads to sustained serum levels of anti-CD47 agent (e.g., an anti-CD47 antibody) that range from about 40 μg/ml to about 300 ug/ml (e.g., from about 40 ug/ml to about 250 ug/ml, from about 40 ug/ml to about 200 ug/ml, from about 40 ug/ml to about 150 ug/ml, from about 40 ug/ml to about 100 ug/ml, from about 50 ug/ml to about 300 ug/ml, from about 50 ug/ml to about 250 ug/ml, from about 50 ug/ml to about 200 ug/ml, from about 50 ug/ml to about 150 ug/ml, from about 75 ug/ml to about 300 ug/ml from about 75 ug/ml to about 250 ug/ml, from about 75 ug/ml to about 200 ug/ml, from about 75 ug/ml to about 150 ug/ml, from about 100 ug/ml to about 300 ug/ml, from about 100 ug/ml to about 250 ug/ml, or from about 100 ug/ml to about 200 ug/ml). In some embodiments, a therapeutically effective dose for treating solid tumors leads to sustained serum levels of anti-CD47 agent (e.g., an anti-CD47 antibody) of about 100 μg/ml or more (e.g., sustained serum levels that range from about 100 ug/ml to about 200 ug/ml). In some embodiments, a therapeutically effective dose for treating non-solid tumors (e.g., acute myeloid leukemia (AML)) leads to sustained serum levels of anti-CD47 agent (e.g., an anti-CD47 antibody) of about 50 μg/ml or more (e.g., sustained serum levels of 75 μg/ml or more; or sustained serum levels that range from about 50 ug/ml to about 150 ug/ml).

Accordingly, a single therapeutically effective dose or a series of therapeutically effective doses would be able to achieve and maintain a serum level of anti-CD47 agent. A therapeutically effective dose of an anti-CD47 agent can depend on the specific agent used, but is usually about 8 mg/kg body weight or more (e.g., about 8 mg/kg or more, about 10 mg/kg or more, about 15 mg/kg or more, about 20 mg/kg or more, about 25 mg/kg or more, about 30 mg/kg or more, about 35 mg/kg or more, or about 40 mg/kg or more), or from about 10 mg/kg to about 40 mg/kg (e.g., from about 10 mg/kg to about 35 mg/kg, or from about 10 mg/kg to about 30 mg/kg). The dose required to achieve and/or maintain a particular serum level is proportional to the amount of time between doses and inversely proportional to the number of doses administered. Thus, as the frequency of dosing increases, the required dose decreases. The optimization of dosing strategies will be readily understood and practiced by one of ordinary skill in the art.

A sub-therapeutic dose is a dose (i.e., an amount) that is not sufficient to affect the desired clinical results. For example, a sub-therapeutic dose of an anti-CD47 agent is an amount that is not sufficient to palliate, ameliorate, stabilize, reverse, prevent, slow or delay the progression of the disease state (e.g., cancer, infection, inflammation, etc.). In some cases, it is desirable to use a sub-therapeutic dose of an anti-CD47 agent as a primer agent (described in more detail below). While the use of a sub-therapeutic dose of an anti-CD47 agent as a primer agent achieves a desired outcome (e.g., the subject is "primed" to receive a therapeutically effective dose), the dose is not considered to be a "therapeutic dose" because the sub-therapeutic dose does not effectively increase phagocytosis of a target cell and is not sufficient to palliate, ameliorate, stabilize, reverse, prevent, slow or delay the progression of the disease state. A sub-therapeutic dose of an anti-CD47 agent can depend on the specific agent used, but is generally less than about 10 mg/kg.

A "maintenance dose" is a dose intended to be a therapeutically effective dose. For example, in experiments to determine the therapeutically effective dose, multiple different maintenance doses may be administered to different subjects. As such, some of the maintenance doses may be therapeutically effective doses and others may be sub-therapeutic doses.

Primer agent. As used herein, the term "primer agent" refers to an agent that primes a subject for a future administration of a therapeutically effective dose of anti-CD47 agent. The inventors have discovered that when a therapeutically effective dose of anti-CD47 agent is administered to a subject without first administering a primer agent, the high required dose can cause a dose-dependent loss of erythrocytes (red blood cells, RBCs) (e.g., as shown below in mice and non-human primate (NHP) models). One of ordinary skill in the art will readily understand how to measure the loss of RBCs. For example, the loss of RBCs can be monitored, for example, by measuring the percent change in hematocrit over time and/or by measuring hemoglobin (e.g., percent change over time, g/dL, etc.) over time (FIG. 1-FIG. 3 and FIG. 7-FIG. 9). The severity of the anemia caused by the loss of RBCs (lethal in some cases) can therefore preclude the use of a therapeutically effective dose of anti-CD47 agent. However, by administering a primer agent prior to administering a therapeutically effective dose of anti-CD47 agent, the subject experiences no adverse effects beyond a temporary, mild anemia that can occur following administration of the primer agent. Thus, administration of a primer agent serves to prime a subject for a future administration of a therapeutically effective dose of anti-CD47.

Subject methods that use a primer agent are particularly relevant when treating primates because primates are sensitive to RBC count and are prone to develop anemia. Thus, in some embodiments, the subject is a primate (e.g., human, prosimians, simians, lemurs, lorisoids, tarsiers, monkeys, apes, capuchin monkeys, howler monkeys, squirrel monkeys, baboons, macaques, gibbons, great apes, and the like).

A primer agent increases the number of RBCs in a subject and thereby counteracts the loss of RBCs caused by the administration of a therapeutically effective dose of anti-CD47 agent. Thus, in some embodiments, a primer agent is an erythropoiesis-stimulating agent (ESA). ESAs are known in the art and include, but are not limited to erythropoietin (EPO), EPO derivatives, and EPO-stimulating compounds. Suitable examples include but are not limited to: EPO alpha, EPO beta, EPO delta, EPO omega, EPO zeta, Darbepoetin alfa (Aranesp), Epoetin alfa (Procrit), Epocept (Lupin pharma), Nanokine (Nanogen Pharmaceutical biotechnology, Vietnam), Epof it (Intas pharma), Epogen (Amgen), Epogin, Eprex, (Janssen-Cilag), NeoRecormon (Hoffmann-La Roche), Recormon, Methoxy polyethylene glycol-epoetin beta (Mircera)(Roche), Dynepo, Epomax, Silapo (Stada), Retacrit (Hospira), Epocept (Lupin Pharmaceuticals), EPOTrust (Panacea Biotec Ltd.), Erypro Safe (Biocon Ltd.), Repoitin (Serum Institute of India Limited), Vintor (Emcure Pharmaceuticals), Epofit (Intas pharma), Erykine (Intas Biopharmaceutica), Wepox (Wockhardt Biotech), Espogen (LG life sciences), ReliPoietin (Reliance Life Sciences), Shanpoietin (Shantha Biotechnics Ltd.), Zyrop Cadila (Healthcare Ltd.), EPIAO (rHuEPO), and (Shenyang Sunshine Pharmaceutical Co. LTD. China). The dose of ESA that should be administered depends on the nature of the agent that is used, and also depends on numerous subject-specific factors (e.g., age, weight, etc.). Methods of determining an appropriate dose of an ESA are known in the art. In some embodiments, the ESA is administered at a dose according to manufacturer's suggestions and in some cases may be as low as about 50 units/kg, about 100 units/kg or about 150 units/kg of body weight or as high as about 17,000 units/kg of body weight.

In some embodiments, the primer agent comprises a sub-therapeutic dose of an anti-CD47 agent. The inventors have discovered that administration of a sub-therapeutic of an anti-CD47 agent as a primer agent effectively primes the subject for a future administration of a therapeutically effective dose of anti-CD47 agent, preventing severe anemia otherwise associated with the therapeutically effective dose.

Accordingly, the term "priming dose" or as used herein refers to a dose of a primer agent (e.g., an anti-CD47 agent, an ESA, etc.) that primes a subject for administration of a therapeutically effective dose of anti-CD47 agent such that the therapeutically effective dose does not result in a severe loss of RBCs (reduced hematocrit or reduced hemoglobin). The specific appropriate priming dose of an anti-CD47 agent can vary depending on the nature of the agent used and on numerous subject-specific factors (e.g., age, weight, etc.). Examples of suitable priming doses of an anti-CD47 agent include, but are not necessarily limited to a range from about 0.05 mg/kg to about 10 mg/kg (e.g., from about 0.1 mg/kg to about 10 mg/kg, from about 0.1 mg/kg to about 7.5 mg/kg, from about 0.1 mg/kg to about 5 mg/kg, from about 0.1 mg/kg to about 4 mg/kg, from about 0.1 mg/kg to about 3 mg/kg, from about 0.5 mg/kg to about 10 mg/kg, from about 0.5 mg/kg to about 7.5 mg/kg, from about 0.5 mg/kg to about 5 mg/kg, from about 0.5 mg/kg to about 4 mg/kg, from about 0.5 mg/kg to about 3 mg/kg, from about 1 mg/kg to about 10 mg/kg, from about 1 mg/kg to about 7.5 mg/kg, from about 1 mg/kg to about 5 mg/kg, from about 1 mg/kg to about 4 mg/kg, from about 1 mg/kg to about 3 mg/kg, about 1 mg/kg, about 2 mg/kg, about 3 mg/kg, about 4 mg/kg, about 5 mg/kg, about 7.5 mg/kg, or about 10 mg/kg). In some embodiments, the primer agent comprises a combination of an ESA and a priming dose of an anti-CD47 agent.

A "loading dose" is a dose intended to be a priming dose. For example, in experiments to determine an effective priming dose, multiple different loading doses may be administered to different subjects. As such, some of the loading doses may be priming doses and others may not be priming doses.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides, or binding of a SIRPα polypeptide). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Suitable specific binding members include agents that specifically bind CD47 and/or SIRPα (i.e., anti-CD47 agents), or that otherwise block the interaction between CD47 and SIRPα.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells.

The term "sample" with respect to a patient encompasses blood and other liquid samples of biological origin, solid tissue samples such as a biopsy specimen or tissue cultures or cells derived or isolated therefrom and the progeny thereof. The definition also includes samples that have been manipulated in any way after their procurement, such as by treatment with reagents; washed; or enrichment for certain cell populations, such as cancer cells. The definition also includes samples that have been enriched for particular types of molecules, e.g., nucleic acids, polypeptides, etc.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample comprising target cells or normal control cells or suspected of comprising such cells or biological fluids derived therefrom (e.g., cancerous cell, infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell from a patient can also include non-inflicted cells.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Methods

Methods are provided for treating a subject with a therapeutic dose of anti-CD47 agent. The subject methods include a step of administering a primer agent to subject, followed by a step of administering a therapeutically effective dose of an anti-CD47 agent to the subject. In some embodiments, the step of administering a therapeutically effective dose is performed after at least about 3 days (e.g., at least about 4 days, at least about 5 days, at least about 6 days, at least about 7 days, at least about 8 days, at least about 9 days, or at least about 10 days) after beginning the administration of a primer agent. This period of time is, for example, sufficient to provide for enhanced reticulocyte production by the individual.

In some embodiments, the step of administering a therapeutically effective dose is performed in a range from about 3 days to about 21 days (e.g., about 3 days to about 17 days, about 3 days to about 14 days, about 3 days to about 12 days, about 4 days to about 12 days, about 5 days to about 12 days, about 5 days to about 11 days, about 5 days to about 10 days, about 5 days to about 9 days, about 6 days to about 8 days, about 3 days, about 4 days, about 5 days, about 6 days, about 7 days, about 8 days, about 9 days, about 10 days, about 11 days, or about 12 days) after beginning the administration of a primer agent. This period of time is, for example, sufficient to provide for enhanced reticulocyte production by the individual.

In some embodiments, two or more primer agents are administered prior to administering a therapeutically effective dose of an anti-CD47 agent. In such cases, the primer agents can be the same agent or can be different agents. The first primer agent can be administered at the same dose or at a different dose as any subsequently administered primer agent. In some embodiments, two or more primer agents are administered simultaneously and/or the administration of two or primer agents overlap in time, where the administration of one may begin or end before or after another primer agent.

The administration of a therapeutically effective dose of an anti-CD47 agent can be achieved in a number of different ways. In some cases, two or more therapeutically effective doses are administered after a primer agent is administered. Suitable administration of a therapeutically effective dose can entail administration of a single dose, or can entail administration of doses daily, semi-weekly, weekly, once every two weeks, once a month, annually, etc. In some cases, a therapeutically effective dose is administered as two or more doses of escalating concentration (i.e., increasing doses), where (i) all of the doses are therapeutic doses, or where (ii) a sub-therapeutic dose (or two or more sub-therapeutic doses) is initially given and therapeutic doses are achieved by said escalation. As one non-limiting example to illustrate escalating concentration (i.e., increasing doses), a therapeutically effective dose can be administered weekly, beginning with a sub-therapeutic dose (e.g., a dose of 5 mg/kg), and each subsequent dose can be increased by a particular increment (e.g., by 5 mg/kg), or by variable increments, until a therapeutic dose (e.g., 30 mg/kg) is reached, at which point administration may cease or may continue (e.g., continued therapeutic doses, e.g., doses of 30 mg/kg). As another non-limiting example to illustrate escalating concentration (i.e., increasing doses), a therapeutically effective dose can be administered weekly, beginning with a therapeutic dose (e.g., a dose of 10 mg/kg), and each subsequent dose can be increased by a particular increment (e.g., by 10 mg/kg), or by variable increments, until a therapeutic dose (e.g., 30 mg/kg, 100 mg/ml, etc.) is reached, at which point administration may cease or may continue (e.g., continued therapeutic doses, e.g., doses of 30 mg/kg, 100 mg/ml, etc.). In some embodiments, administration of a therapeutically effective dose can be a continuous infusion and the dose can altered (e.g., escalated) over time.

Dosage and frequency may vary depending on the half-life of the anti-CD47 agent in the patient. It will be understood by one of skill in the art that such guidelines will be adjusted for the molecular weight of the active agent, e.g. in the use of antibody fragments, in the use of antibody conjugates, in the use of SIRPα reagents, in the use of soluble CD47 peptides etc. The dosage may also be varied for localized administration, e.g. intranasal, inhalation, etc., or for systemic administration, e.g. i.m., i.p., i.v., and the like.

Effective administration of primer agent. In some embodiments, a step of determining whether administration of the primer agent was effective is performed prior to the step of administering a therapeutically effective dose of an anti-CD47 agent to the subject. If the administration of the primer agent was not effective, then it may be desirable to begin anew and again administer a primer agent. In such a case, a different dose and/or a different primer agent may be used, or the same dose and same primer agent may be used. If the administration of the primer agent was effective (i.e., the reticulocyte count indicates that the administration was effective, as described below in more detail), then a therapeutically effective dose of an anti-CD47 agent can be delivered.

Because a priming dose of a primer agent may increase the number of RBCs in a subject (which occurs after administering ESA primer agents as well as after administering priming doses of anti-CD47 agents), evaluation of recently produced (i.e., young) blood cells (i.e., reticulocytes) can serve as an evaluation tool for determining whether administration of the primer agent was effective.

Methods of evaluating reticulocytes include measuring the absolute or relative number of reticulocytes in a blood sample (e.g., a reticulocyte count can be performed on a blood sample from a subject prior to and following administration of a primer agent). Methods to evaluate and/or count reticulocytes are known by one of ordinary skill in the art and any convenient method may be used. An example of a suitable method includes, but is not limited to counting the number of reticulocytes in a sample based on a morphological evaluation. Reticulocytes exhibit a mesh-like network that becomes visible with particular stains, e.g., new methylene blue (NMB). Reticulocytes appear slightly bluer than other red cells when looked at with the normal Romanowsky stain. Reticulocytes are also slightly larger, which can be picked up as a high MCV (mean corpuscular volume) with a full blood count.

Another example of a suitable method to evaluate reticulocytes includes, but is not limited to counting the number of reticulocytes based on the expression of a marker of young/immature RBCs (e.g., CD71 expression is increased in young RBCs relative to older RBCs and CD71 can serve as a marker to identify reticulocytes).

Another example of a suitable method to evaluate reticulocytes includes, but is not limited to counting the number of reticulocytes in a sample based on measuring the amount of fluorescence exhibited by cells after contacting the samples with a fluorescent dye (e.g., thiazole orange, polymethine, etc.) that marks nucleic acid (RNA and DNA), and is therefore a non-selective nucleic acid dye. For example, a non-selective nucleic acid dye can stain reticulocytes' residual RNA while a DNA-selective dye (e.g., DRAQ5), which can be used in conjunction with a non-selective nucleic acid dye (e.g., thiazole orange), will not stain reticulocytes because reticulocytes have no DNA (reticuloctyes are therefore DRAQ5 negative). A comparatively middle level of fluorescence distinguishes reticulocytes from mature RBCs (which have neither RNA nor DNA, and therefore very little fluorescence) and from lymphocytes (which have a large amount of DNA, unlike reticulocytes). Thus, reticulocyte counts can't be performed in an automated manner (e.g., using fluorescence-activated cell sorting (FACS)).

Another example of a suitable method to determine whether administration of the primer agent was effective includes measuring the level of EPO in the blood. While ESAs can be used to directly stimulate EPO production, priming doses of anti-CD47 agents also cause increases in EPO levels. As such, the step of determining whether administration of the primer agent was effective can comprise measuring the level of EPO in the blood (e.g., prior to and following administration of a primer agent).

Another example of a suitable method to determine whether administration of the primer agent was effective includes measuring hemoglobin. Methods to measure hemoblobin are known by one of ordinary skill in the art and any convenient method may be used. Hemoglobin is usually measured as a part of the complete blood count (CBC) from a blood sample. Laboratory hemoglobin test methods require a blood sample (arterial, venous, or capillary) and analysis on a hematology analyzer and CO-oximeter. Additionally, noninvasive hemoglobin test methods (e.g., Pulse CO-Oximetry) may be used. As one non-limiting example of measuring hemoglobin, red blood cells are broken down to get hemoglobin into solution. The free hemoglobin is exposed to a chemical containing cyanide, which binds tightly with the hemoglobin molecule to form cyanmethemoglobin. By exposing the sample a specific wavelength of light (e.g., 540 nm) the amount of hemoglobin can be determined.

Determining whether the administration of a primer agent was effective (e.g., via a reticulocyte count) can be performed in a range from about 3 days to about 12 days (e.g., about 4 days to about 11 days, about 5 days to about 10 days, about 6 days to about 10 days, about 7 days to about 9 days, about 3 days, about 4 days, about 5 days, about 6 days, about 7 days, about 8 days, about 9 days, about 10 days, about 11 days, or about 12 days) after beginning step (a).

When a reticulocyte count is performed, a count of about $400 \times 10^9$ reticulocytes/L or more indicates that the administration of the primer agent was effective. Reticulocyte counts are often expressed as a percentage of red blood cells that are reticulocytes and a normal count for a healthy adult ranges from 0.5% to 2%. When reticulocyte counts are expressed in this way, a value of about 4% or more (e.g., 4.5% or more, 5% or more, 5.5% or more, or 6 or more) indicates that the administration of the primer agent was effective. In some cases, a fold-increase in reticulocyte number can be calculated and an increase of 2-fold or more (e.g., 3-fold or more, 3.5-fold or more, 4-fold or more, 4.5-fold or more, or 5-fold or more) indicates that the administration of the primer agent was effective. When a hemoglobin measurement is performed, an absolute decrease of about 2 to about 4 g/dL or a relative decrease of about 12% or more (e.g. about 15% or more, 17.5% or more, 20% or more, 25% or more, or 30% or more), or a relative decrease ranging from about 12% to about 30% (e.g., about 15% to about 30%, about 15% to about 25%, or about 20% to about 30%) indicates that the administration of the primer agent was effective.

In some embodiments, a subject is monitored for clinical signs of disease (e.g., cancer or infection) following administration of a therapeutically effective dose of an anti-CD47 agent.

Kits

Also provided are kits for use in the methods. The subject kits include a primer agent and an anti-CD47 agent. In some embodiments, a kit comprises two or more primer agents. In some embodiments, a kit comprises two or more anti-CD47 agents. In some embodiments, a primer agent is provided in a dosage form (e.g., a priming dosage form). In some embodiments, a primer agent is provided in two or more different dosage forms (e.g., two or more different priming dosage forms). In some embodiments, an anti-CD47 agent is provided in a dosage form (e.g., a therapeutically effective dosage form). In some embodiments, an anti-CD47 agent is provided in two or more different dosage forms (e.g., two or more different therapeutically effective dosage forms). In the context of a kit, a primer agent and/or an anti-CD47 agent can be provided in liquid or sold form in any convenient packaging (e.g., stick pack, dose pack, etc.).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Utility. The subject methods and kits can be used to treat any infliction where the target cells (e.g., cancer cells, infected cells, etc.) exhibit an increased expression of CD47 relative to normal cells of the same type. The anti-CD47 agent that is administered inhibits the interaction between SIRPα (e.g., on a phagocyte) and CD47 on an target cell (e.g., on a cancer cell, on an infected cell, etc.), thereby increasing in vivo phagocytosis of the target cell. Subject methods include administering to a subject in need of treatment a therapeutically effective dose of an anti-CD47 agent, including without limitation combinations of the reagent with another drug (e.g., an anti-cancer drug, an anti-infection drug, etc.).

In some embodiments the infliction is a chronic infection, i.e. an infection that is not cleared by the host immune system within a period of up to 1 week, 2 weeks, etc. In some cases, chronic infections involve integration of pathogen genetic elements into the host genome, e.g. retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses.

Viral pathogens of interest include without limitation, retroviral and lentiviral pathogens, e.g. HIV-1; HIV-2, HTLV, FIV, SIV, etc. Hepatitis B virus, etc. Microbes of interest, but not limited to the following, include: *Yersinia* sp., e.g. *Y. pestis, Y. pseudotuberculosis, Y enterocolitica; Franciscella* sp.; *Pasteurella* sp.; *Vibrio* sp., e.g. *V. cholerae, V. parahemolyticus; Legionella* sp., e.g. *L. pneumophila; Listeria* sp., e.g. *L. monocytogenes; Mycoplasma* sp., e.g. *M. hominis, M. pneumoniae; Mycobacterium* sp., e.g. *M. tuberculosis, M. leprae; Rickettsia* sp., e.g. *R. rickettsii, R. typhi; Chlamydia* sp., e.g. *C. trachomatis, C. pneumoniae, C. psittaci; Helicobacter* sp., e.g. *H. pylori*, etc. Also included are intracellular protozoan pathogens, e.g. *Plasmodium* sp, *Trypanosoma* sp., *Giardia* sp., *Toxoplasma* sp., *Leishmania* sp., etc.

An infection treated with the methods of the invention generally involves a pathogen with at least a portion of its life-cycle within a host cell, i.e. an intracellular phase. The methods of the invention provide for a more effective removal of infected cells by the phagocytic cells of the host organism, relative to phagocytosis in the absence of treatment, and thus are directed to the intracellular phase of the pathogen life cycle.

In some embodiments, the methods of the invention involve diagnosis of a patient as suffering from a pathogenic intracellular infection; or selection of a patient previously diagnosed as suffering from a pathogenic intracellular infection; treating the patient with a regimen of anti-CD47 therapy, optionally in combination with an additional therapy; and monitoring the patient for efficacy of treatment. Monitoring may measure clinical indicia of infection, e.g. fever, white blood cell count, etc., and/or direct monitoring for presence of the pathogen.

Treatment may be combined with other active agents. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenicol; metronidazole; spectinomycin; trimethoprim; vancomycin; etc. Cytokines may also be included, e.g. interferon γ, tumor necrosis factor α, interleukin 12, etc. Antiviral agents, e.g. acyclovir, gancyclovir, etc., may also be used in treatment.

In some embodiments the infliction is cancer. As noted above, any cancer in which a cancerous cell expresses an increased level of CD47 relative to a non-cancerous cell of the same type can be treated with the subject methods.

The term "cancer", as used herein, refers to a variety of conditions caused by the abnormal, uncontrolled growth of cells. Cells capable of causing cancer, referred to as "cancer cells", possess characteristic properties such as uncontrolled proliferation, immortality, metastatic potential, rapid growth and proliferation rate, and/or certain typical morphological features. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer, and detecting a genotype indicative of a cancer. However, a negative result in one or more of the above detection methods does not necessarily indicate the absence of cancer, e.g., a patient who has exhibited a complete response to a cancer treatment may still have a cancer, as evidenced by a subsequent relapse.

The term "cancer" as used herein includes carcinomas, (e.g., carcinoma in situ, invasive carcinoma, metastatic carcinoma) and pre-malignant conditions, i.e. neomorphic changes independent of their histological origin. The term "cancer" is not limited to any stage, grade, histomorphological feature, invasiveness, aggressiveness or malignancy of an affected tissue or cell aggregation. In particular stage 0 cancer, stage I cancer, stage II cancer, stage III cancer, stage IV cancer, grade I cancer, grade II cancer, grade III cancer, malignant cancer and primary carcinomas are included.

Cancers and cancer cells that can be treated include, but are not limited to, hematological cancers, including leukemia, lymphoma and myeloma, and solid cancers, including for example tumors of the brain (glioblastomas, medulloblastoma, astrocytoma, oligodendroglioma, ependymomas), carcinomas, e.g. carcinoma of the lung, liver, thyroid, bone, adrenal, spleen, kidney, lymph node, small intestine, pancreas, colon, stomach, breast, endometrium, prostate, testicle, ovary, skin, head and neck, and esophagus.

In an embodiment, the cancer is a hematological cancer. In an embodiment, the hematological cancer is a leukemia. In another embodiment, the hematological cancer is a myeloma. In an embodiment, the hematological cancer is a lymphoma.

In an embodiment, the leukemia is selected from acute myeloid leukemia (AML), acute lymphocytic leukemia (ALL), chronic lymphocytic leukemia (CLL) and chronic myelogenous leukemia (CML). In an embodiment, the leukemia is AML. In an embodiment, the leukemia is ALL. In an embodiment, the leukemia is CLL. In a further embodiment, the leukemia is CML. In an embodiment, the cancer cell is a leukemic cell, for example, but not limited to, an AML cell, an ALL cell, a CLL cell or a CML cell.

Suitable cancers responsive to treatment using an anti-CD47 agent include without limitation leukemia; acute myeloid leukemia (AML); acute lymphoblastic leukemia (ALL); metastasis; minimal residual disease; solid tumor cancers, e.g., breast, bladder, colon, ovarian, glioblastoma, leiomyosarcoma, and head & neck squamous cell carcinomas; etc. For examples, see: (i) Willingham et al., Proc Natl Acad Sci USA. 2012 Apr. 24; 109(17):6662-7: "The CD47-signal regulatory protein alpha (SIRPα) interaction is a therapeutic target for human solid tumors"; (ii) Edris et al., Proc Natl Acad Sci USA. 2012 Apr. 24; 109(17):6656-61: "Antibody therapy targeting the CD47 protein is effective in a model of aggressive metastatic leiomyosarcoma"; and (iii) US patent application 20110014119; all of which are herein incorporated in their entirety.

Pharmaceutical Compositions. Suitable anti-CD47 agents and/or primer agents can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of an anti-CD47 agent or primer agent includes use in combination with another therapeutic agent (e.g., another anti-infection agent or another anti-cancer agent). Therapeutic formulations comprising one or more anti-CD47 agents and/or primer agents of the invention are prepared for storage by mixing the anti-CD47 agent or primer agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The anti-CD47 agent or primer agent composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The anti-CD47 agent or primer agent can be administered by any suitable means, including topical, oral, parenteral, intrapulmonary, and intranasal. Parenteral infusions include intramuscular, intravenous (bollus or slow drip), intraarterial, intraperitoneal, intrathecal or subcutaneous administration.

The anti-CD47 agent or primer agent need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

An anti-CD47 agent or primer agent is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™' agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an anti-CD47 agent or primer agent by non-covalent associations, such as non-covalent bonding or by encapsulation. The nature of the carrier can be either soluble or insoluble for purposes of the invention. Those skilled in the art will know of other suitable carriers for binding anti-CD47 agents and/or primer agents, or will be able to ascertain such, using routine experimentation.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the methods of the invention. Such moieties may be conjugated to the anti-CD47 agent or primer agent through an acceptable chemical linker or chelation carrier. Positron emitting moieties for use in the present invention include $^{18}F$, which can be easily conjugated by a fluorination reaction with the anti-CD47 agent or primer agent.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the anti-CD47 agents and/or primer agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing a therapeutic dosage range and/or a priming dosage range for use in humans. The exact formulation, route of administration and dosage can be chosen by the individual physician in view of the patient's condition.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

Example 1

Single Injection of Anti-CD47 Antibodies in Wild Type Mice

Figure 1B:
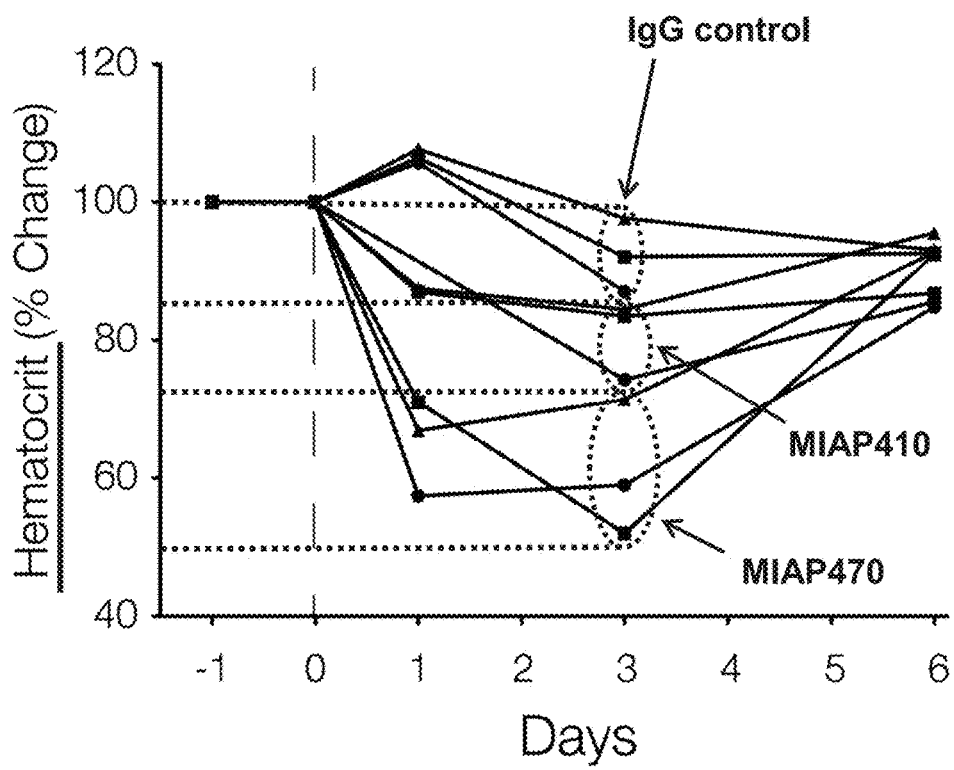

A single 250 µg IP injection of MIAP410 (IgG1 isotype) or MIAP470 (IgG2a isotype) was administered to wild type mice. This antibody dose is roughly equivalent to a 10 mg/kg dose. Blood was collected from retro-orbital plexus and CBC analysis was performed on HemaTrue hematology analyzer 1, 3, and 6 days after antibody injection. The percent change in hematocrit (HCT) and RBC values are shown in FIG. 1. All anti-CD47 mAb treated mice developed anemia, the nadir of which occurred about 3 days after injection. The MIAP470 caused a more significant anemia, which is likely due to differential FcR mediated effects caused by the IgG1 and IgG2a isotypes.

Figure 2:
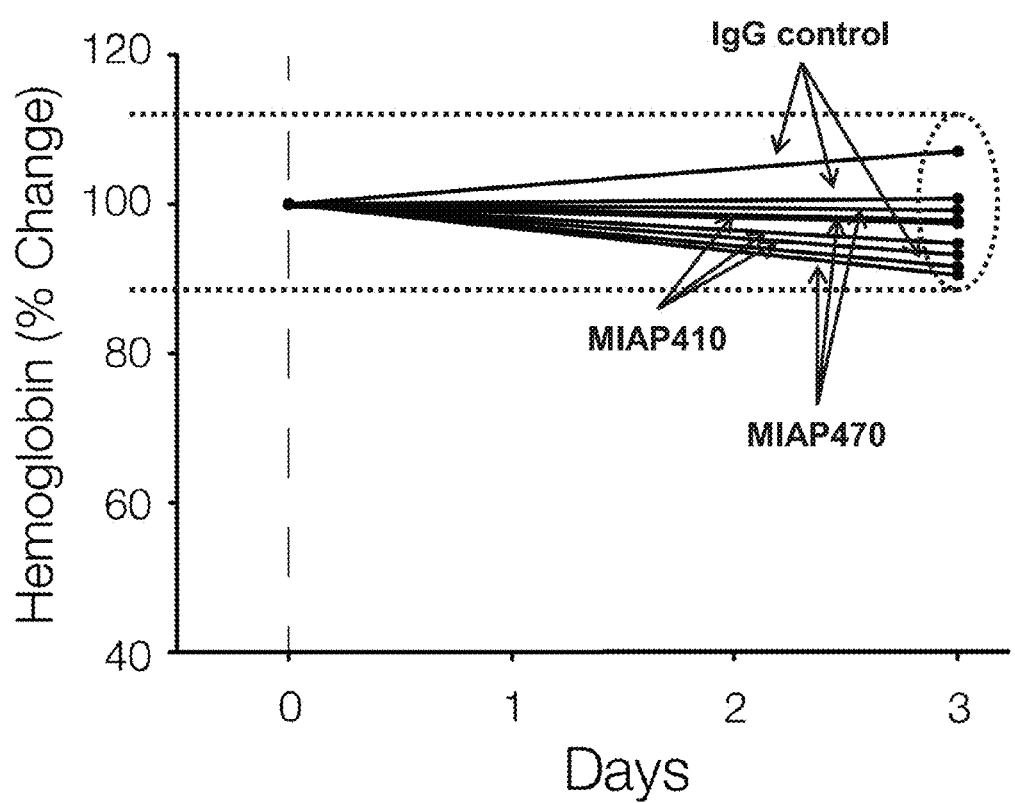
FIG. 2 presents percent change in hemoglobin after a single 250 µg IP injection of MIAP410 (IgG1 isotype) or MIAP470 (IgG2a isotype) was administered to CD47$^{-/-}$ mice.

Single Injection of Anti-CD47 Antibodies in $CD47^{-/-}$ Mice $CD47^{-/-}$ mice were acquired from Jackson Laboratory and injected IP with 250 µg of control mouse IgG, MIAP410, or MIAP470. Blood was collected and analyzed 72 hours after mAb injection. No anemia was observed in any of the injected $CD47^{-/-}$ mice. The percent change in hemoglobin is shown in FIG. 2. This demonstrates that the observed anemia in wild type mice was a direct result of anti-CD47 antibodies binding CD47.

Multiple Injections of Anti-CD47 Antibodies in Wild Type Mice

Figure 3A:
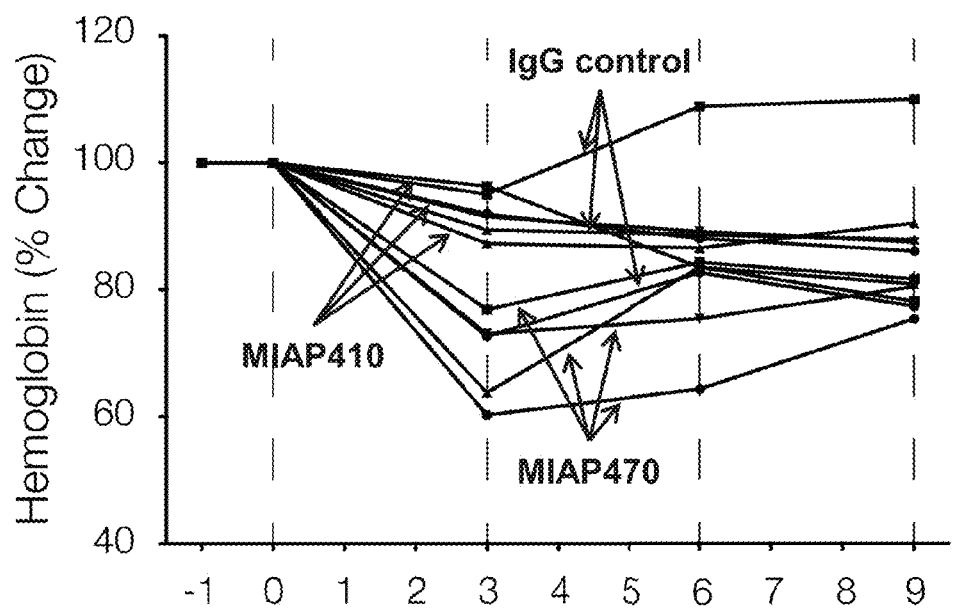
FIG. 3A-3B presents percent change in hematocrit (HCT) and percent change hemoglobin after IP injections of 250 µg of control mouse IgG, MIAP410, or MIAP740 were administered to wild type mice every 3 days.
Figure 3B:
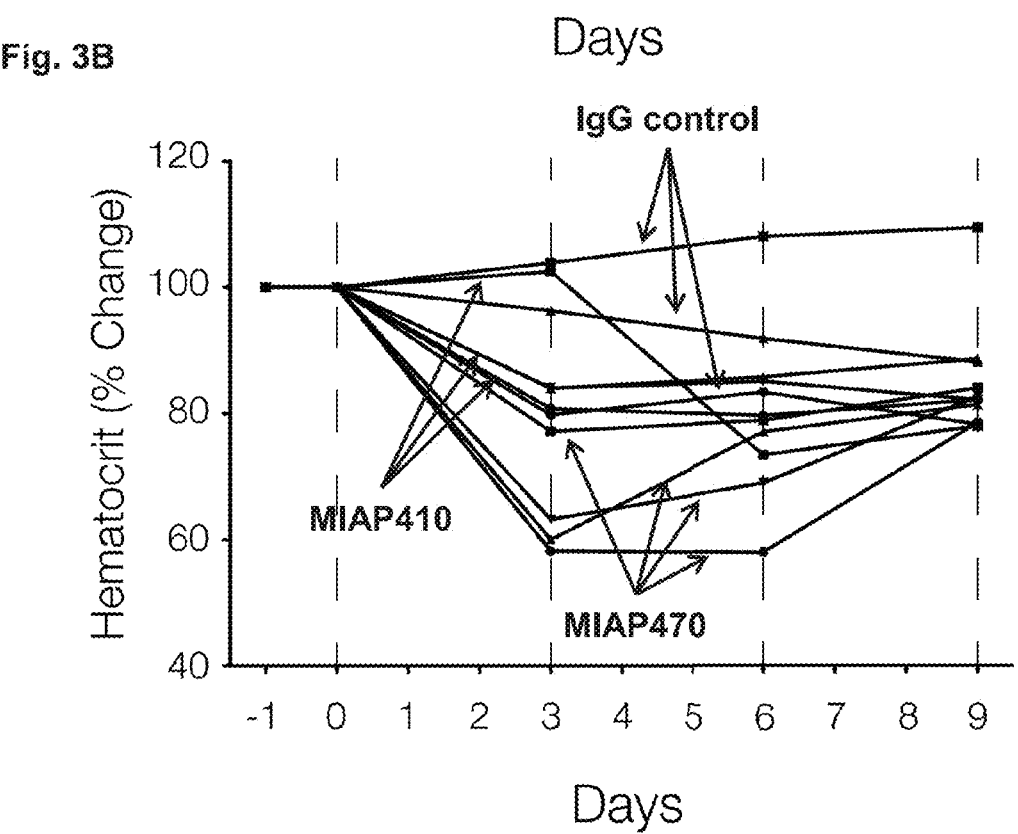

WT mice were given an IP injection of 250 µg of control mouse IgG, MIAP410, or MIAP740 every 3 days (represented by dashed vertical line in FIG. 3). Erythrocyte toxicity was monitored by CBC analysis prior to each injection. An acute drop in HCT occurred upon the first antibody injection (Day 0). The second injection (on day 3) did not result in a further drop in hematocrit. Mice appeared to become resistant to subsequent injections and eventually returned to a range similar to that of control IgG treated mice. The discovery that repeated administration of anti-CD47 antibodies does not exacerbate the initial anemia is the basis of the subsequent experiments in non-human primates.

Example 2

Verification of Dosing Strategy in Non-Human Primates (NHPs)

The Hu5F9-G4 anti-CD47antibody (and its parent 5F9) binds human CD47, but does not bind mouse CD47. In order to identify an appropriate toxicology species, the sequence of macaque (cynomolgus) non-human primate (NHP) CD47 was aligned with human CD47 and it was determined that the two sequences contain only 3 amino acid differences in the extracellular domain (FIG. 4). All 3 non-conserved amino acids are located outside of the SIRP-alpha interacting region as has been determined by published X-ray crystal structures.

Figure 5:
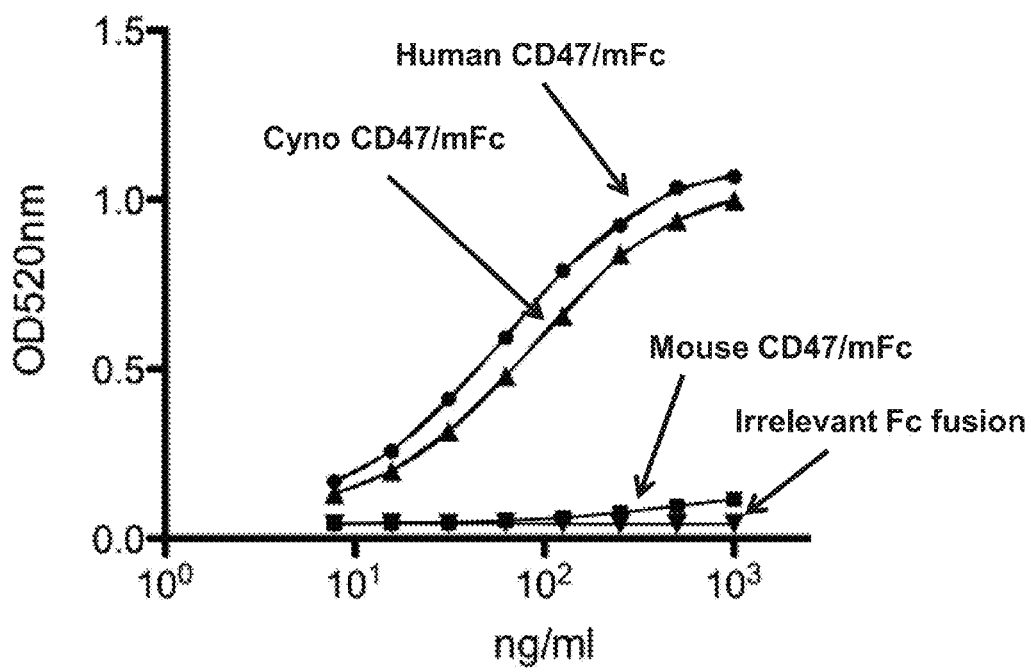
FIG. 5 demonstrates that Hu5F9-G4 recognizes human and cynomolgus CD47, but not mouse CD47. ELISA was performed by coating an anti-mouse Fc specific antibody, followed by adding human, mouse, and cyno CD47-mFc fusion proteins. An irrelevant mouse Fc (mFc) fusion protein was used as a negative control. Hu5F9-G4 was then added. Bound antibody was detected using HRP-conjugated anti-human Kappa antibody.

A cynomolgus NHP CD47-Fc fusion protein was generated and it was determined that Hu5F9-G4 does in fact bind to cynomolgus NHP CD47 (FIG. 5). Surface plasmon resonance (SPR) affinity measurements were further conducted by using Biacore. The results show that Hu5F9-G4 binds cynomolgus CD47 with an affinity comparable to that of human CD47 (FIG. 6).

In addition, flow cytometry and immunofluorescence, respectively, were used to show that Hu5F9-G4 antibody binds cynomolgus NHP leukocytes and normal tissues in a distribution similar to human leukocytes and tissues. Taken together, these studies demonstrated that the cynomolgus monkey is a relevant species for the safety and toxicology studies.

Anti-CD47 Antibodies Causes Dose Dependent Anemia in NHPs (Single Dose)

Figure 7A:
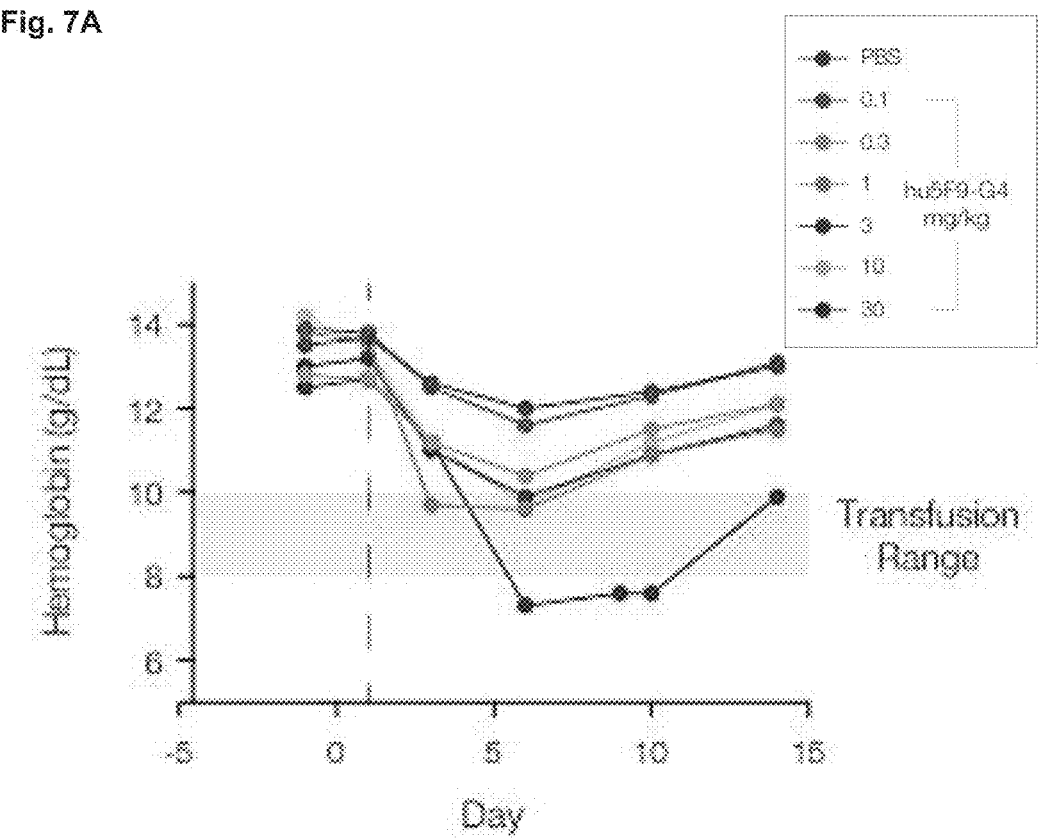
FIG. 7A-7B presents data from Non-Human Primate Hu5F9-G4 toxicokinetic studies. Cynomolgus NHP were administered Hu5F9-G4 by single doses at the indicated levels.
Figure 7B:
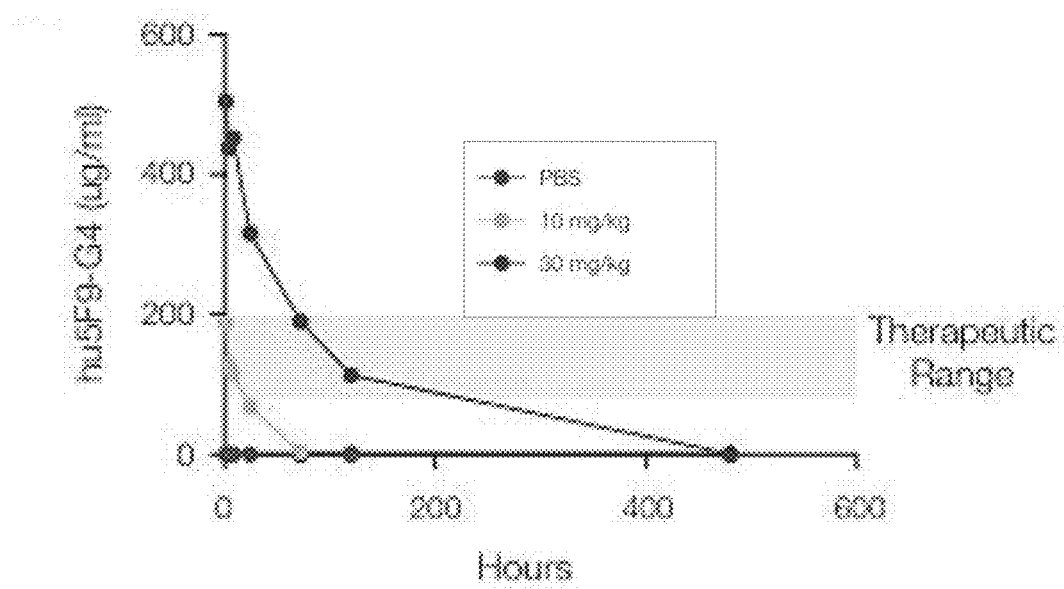

A number of NHP studies were conducted using purified Hu5F9-G4 antibodies produced by Lonza using their proprietary Glutamine Synthetase (GS) expression system. Hu5F9-G4 was administered as a single dose at 0.1, 0.3, 1, 3, 10, or 30 mg/kg and clinical pathology parameters were monitored, including complete blood counts and metabolic panels. A dose-dependent anemia, associated with reticulocytosis and spherocytosis, was observed without hepatic or renal dysfunction (FIG. 7). There was no free plasma hemoglobin detected, indicating the absence of intravascular hemolysis. Monitoring of pharmacokinetics through measurement of serum levels indicated that there is a large antigen sink resulting in a short half-life (FIG. 7). With single doses, only 10 and 30 mg/kg were able to transiently achieve serum levels in the range associated with efficacy in xenograft studies. Thus, proper dosing can achieve and maintain therapeutically effective anti-CD47 agent levels while minimizing anemia.

Escalating Concentrations of Anti-CD47 Antibodies do not Exacerbate Anemia

Figure 8A:
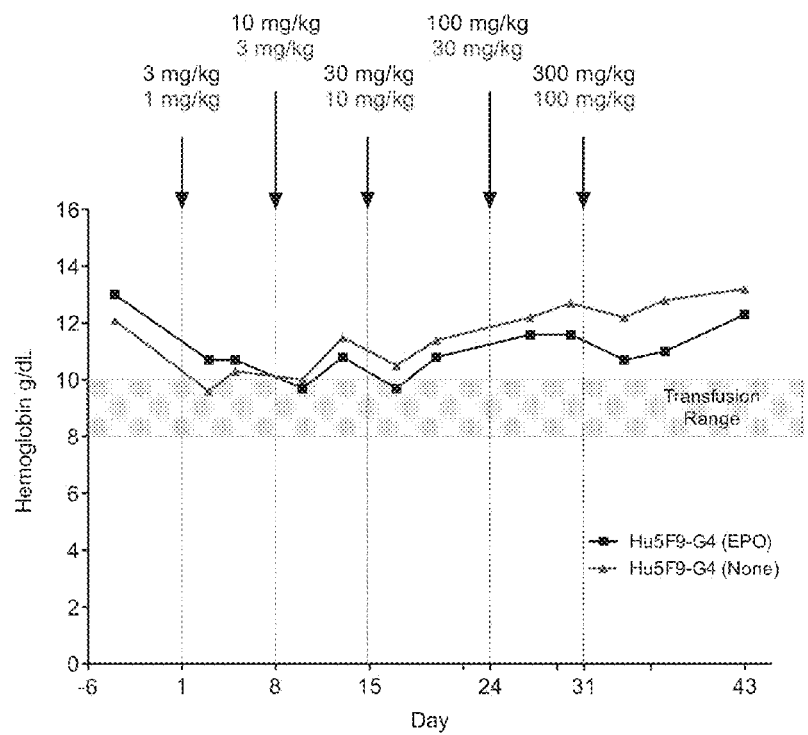
FIG. 8A-8B presents data from a Non-Human Primate Hu5F9-G4 dose escalation toxicokinetic study. Cynomolgus NHP that received either no pre-treatment or pre-treatment with a single dose of EPO were administered Hu5F9-G4 in a dose escalation study with the doses and time points indicated.
Figure 8B:
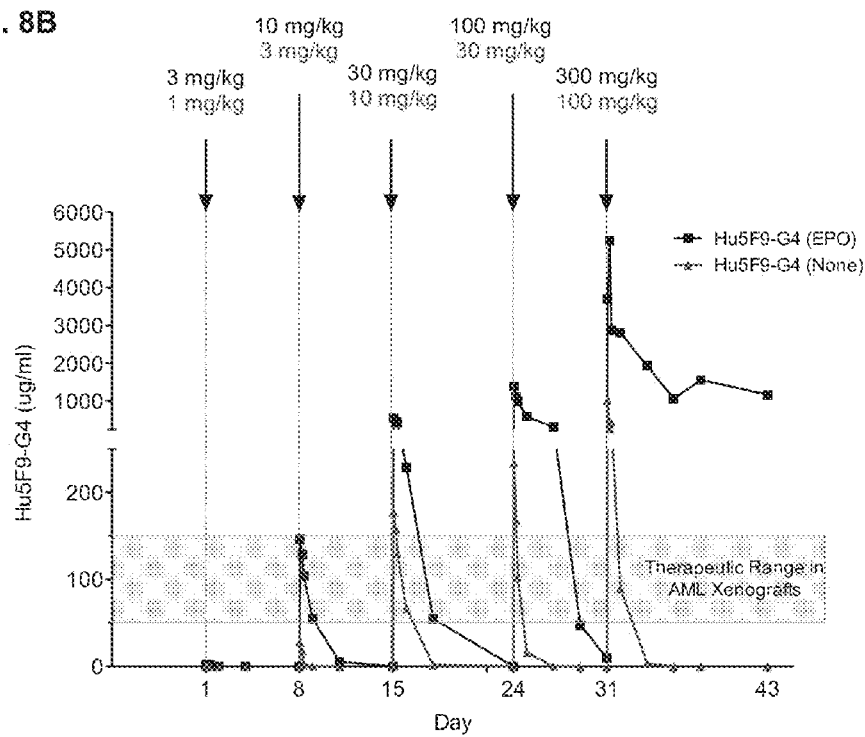

We speculated that prior administration of erythropoietin (EPO) would blunt the anemia by stimulating young RBC production. From these considerations, we conducted a separate dose-escalation study in NHP based on the hypothesis that initial low doses would blunt the loss of aged RBC and stimulate production of less-susceptible young RBC, thereby facilitating tolerance of subsequent larger doses (FIG. 8). Two animals were enrolled into this study and dosed at one week intervals: one with EPO pre-treatment (3, 10, 30, 100, and 300 mg/kg), and one with no pre-treatment (1, 3, 10, 30, and 100 mg/kg). In both cases, the NHP exhibited a mild anemia with initial dosing that did not worsen with repeated administrations. In fact, the hemoglobin only reached the upper threshold for transfusion in humans, even without EPO pretreatment. The animals tolerated all doses well, including 100 and 300 mg/kg, with no additional blood or metabolic abnormalities. At the end of the study, both animals were euthanized, and necropsy and histopathology analysis revealed no abnormalities.

Figure 9A:
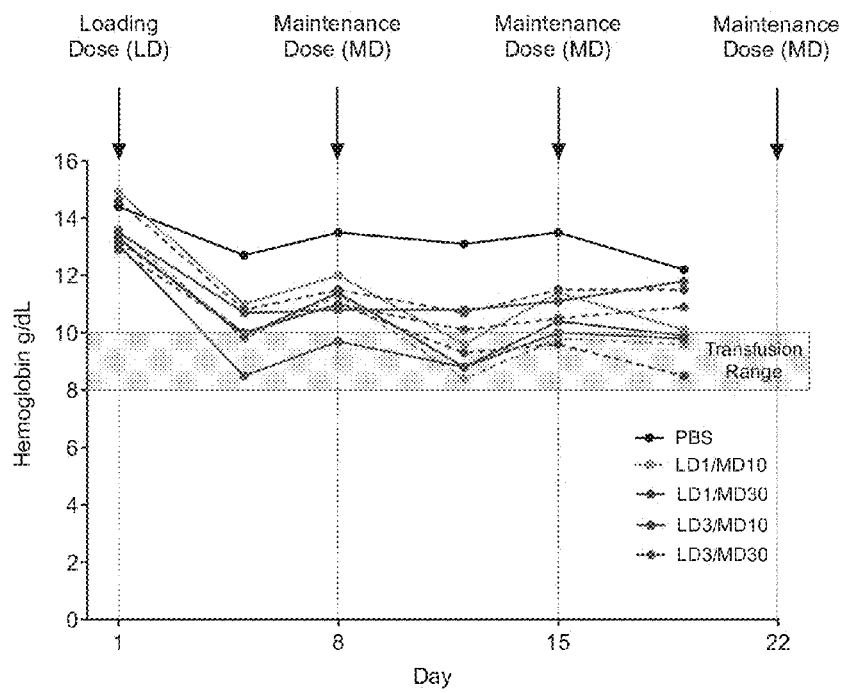
FIG. 9A-9B presents data from a Non-Human Primate Hu5F9-G4 Loading-Maintenance Dose Toxicokinetic Study. Cynomolgus NHP received a loading dose (LD) (i.e., a priming dose) on day 1 of either 1 mg/kg or 3 mg/kg and then maintenance doses (MD) of either 10 or 30 mg/kg at the indicated time points. 2 NHPs (solid line and dashed line) were used in each experimental group.
Figure 9B:
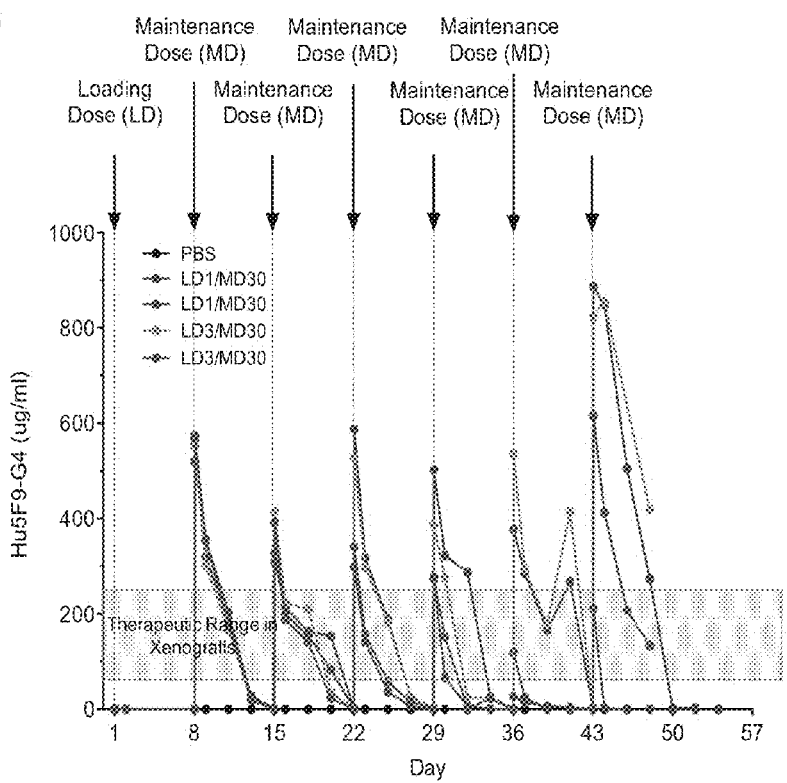

From this dose-escalation study, we determined the pharmacokinetics of Hu5F9-G4 in NHP. Consistent with the presence of a large antigen sink of CD47 expressed by normal tissues, the initial low doses of Hu5F9-G4 were rapidly cleared from the serum with a half-life of 24 hours (FIG. 9). In contrast, the higher doses of Hu5F9-G4 produced sustained serum levels indicating saturation of the antigen sink. The animal dosed at 300 mg/kg had a peak level of 5 mg/ml with a sustained level of more than 1 mg/ml for nearly 2 weeks.

Single Loading Dose of Anti-CD47 Antibodies Enables Higher Maintenance Doses

Figure 10:
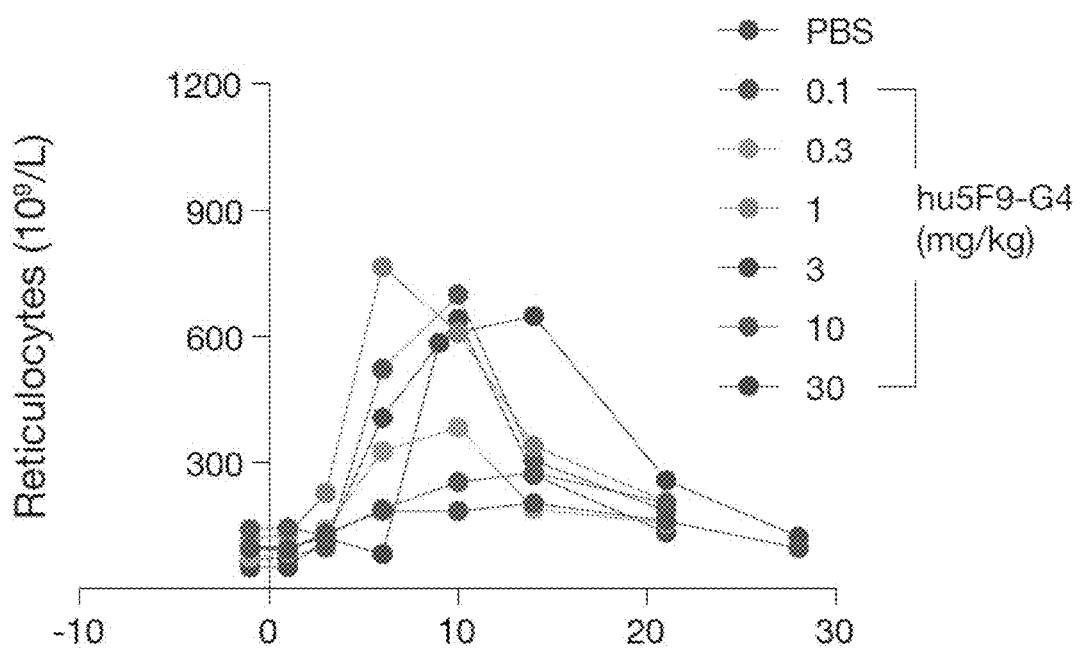
FIG. 10 presents reticulocyte count data demonstrating the level of reticulocytosis associated with various doses of an anti-CD47 agent (hu5F9-G4 antibody in this case).

These studies demonstrated that Hu5F9-G4 can be administered to NHP at doses capable of achieving prolonged, therapeutic serum levels without major toxic effects. To model potential clinical dosing strategies, we have conducted another NHP study using a loading-maintenance dosing approach. In this study, Hu5F9-G4 is administered with a loading dose capable of stimulating mild anemia and reticulocytosis without grade 3 toxicity. Our single dose data (See above), led us to select either 1 or 3 mg/kg on day 1 as the loading dose. One week later, a maintenance dose of either 10 or 30 mg/kg is administered, and continued weekly for 3 doses. Both loading doses mitigate the severity of the anemia, even with the 30 mg/kg maintenance doses, and no grade 3 toxicity develops. PK data following the first maintenance dose indicate that the animals have achieved therapeutic levels. This study suggests that a loading-maintenance strategy mitigates anemia (preventing grade 3 toxicity) while achieving potentially therapeutic drug levels. FIG. 10 presents reticulocyte count data demonstrating the level of reticulocytosis associated with various doses of an anti-CD47 agent (hu5F9-G4 antibody in this case).

Example 3

Therapeutic Efficacy of Anti-CD47 Antibodies in Xeno-transplantation Assays

We previously reported preclinical evidence that a blocking anti-CD47 monoclonal antibody (clone B6H12, mouse IgG1) was effective at inhibiting the growth and metastasis of solid tumors, including breast, bladder, colon, ovarian, glioblastoma, leiomyosarcoma, and head & neck squamous cell carcinoma (PMID: 22451913, 22451919). Anti-CD47 monoclonal antibodies also caused similar inhibition of hematologic tumor growth (PMID: 21177380, 20813259, 19632179, 19632178). We have now confirmed that humanized antibodies (e.g., the humanized anti-CD47 antibody used in the studies above, hu5F9-G4) is also highly effective at inhibiting solid tumor growth and eliminating metastases (FIG. 11).

To investigate the efficacy of hu5F9-G4 on solid tumors, a human bladder cancer cell line (639V) was subcutaneously transplanted into immunodeficient mice. Tumor bearing mice were treated with PBS or hu5F9-G4. Due to tumor burden, all PBS-treated mice were euthanized after 4 weeks of treatment. In contrast, no tumor growth was observed in the hu5F9-G4 treated cohort (FIG. 11). These mice we then monitored for an additional 4 weeks (without further hu5F9-G4 treatment). No tumor growth was observed in mice that had been treated hu5F9-G4, indicating that the tumors had been fully eliminated (FIG. 11A).

To evaluate the effect of hu5F9-G4 on formation of tumor metastases, we subcutaneously engrafted a human metastatic prostate tumor specimen into immunodeficient mice. Upon tumor engraftment, we initiated treatment with PBS or hu5F9-G4. After 6 weeks of treatment, a significant decrease in the number and size of lymph node metastases was observed (FIG. 11B). These results indicate that hu5F9-G4 can inhibit or eliminate tumor metastases.

Figure 12B:
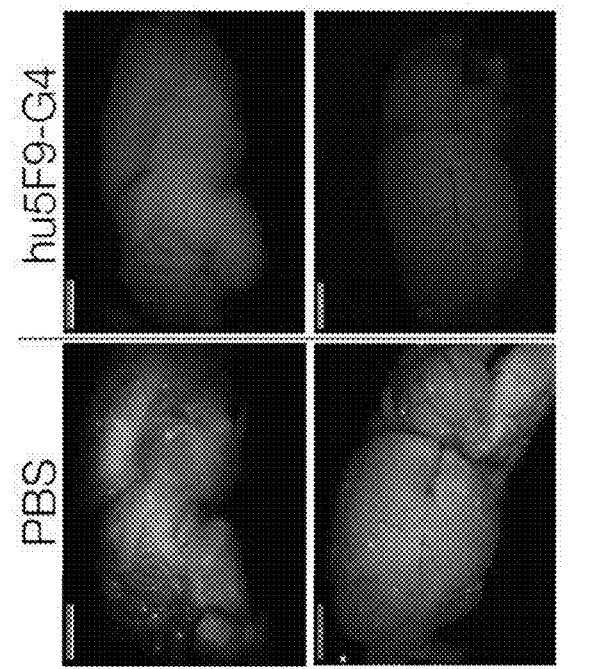
FIG. 12A-12D demonstrates that Hu5F9-G4 eliminates established metastases.
Figure 12A:
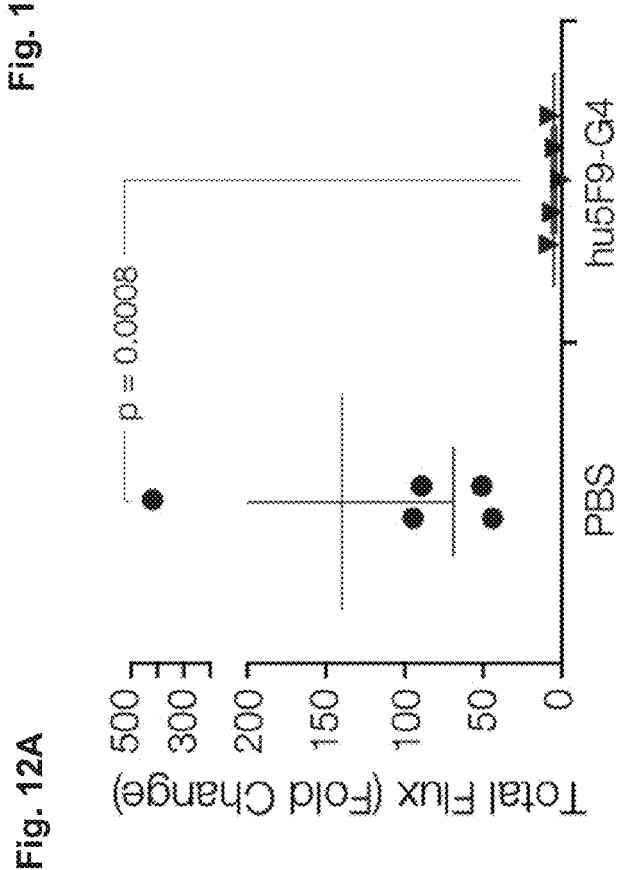
Figures 12C, 12D:
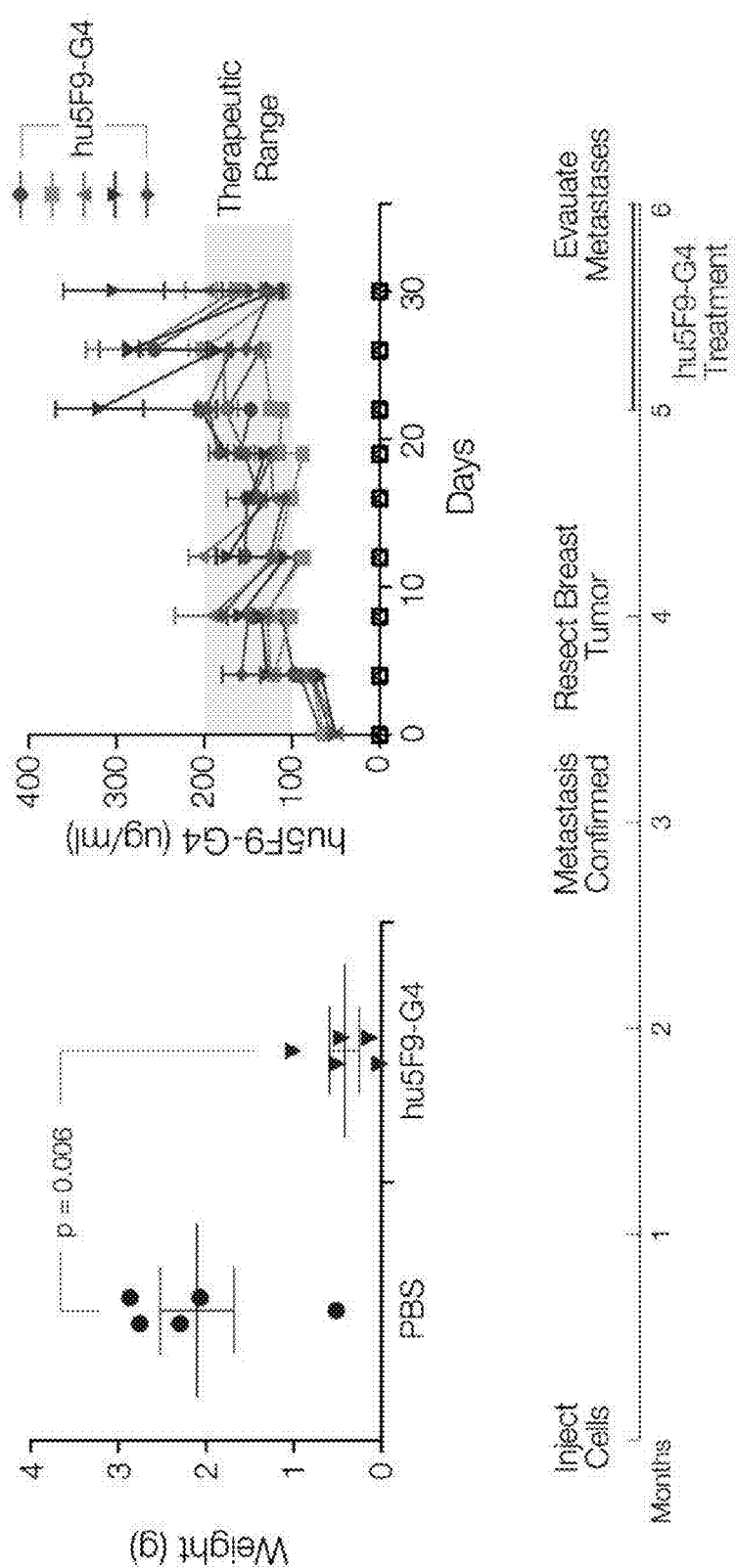

To demonstrate the potential of hu5F9-G4 to eliminate established metastases, we engrafted primary human breast cancer cells into the mouse mammary fat pad. After confirming the presence of tumor metastases in the lungs, we resected the primary tumor and initiated treatment with PBS or hu5F9-G4. After 4 weeks, a significant inhibition of lung metastasis growth was observed in hu5F9-G4 treated mice (FIG. 12A). Moreover, a complete elimination of tumor metastases in the brain was observed (FIG. 12B). Hu5F9-G4 also inhibited the regrowth of the resected primary tumor, indicating that hu5F9-G4 is also be effective in treating minimal residual disease (FIG. 12C).

Serum concentrations of hu5F9-G4 were monitored throughout the experiment. Hu5F9-G4 concentrations between 100-200 µg/ml were associated with therapeutic efficacy (FIG. 12AD). These data demonstrate that humanized antibodies (e.g., hu5F9-G4), have the same general properties related to the treatment of disease (e.g., cancer or chronic infection) as the non-humanized antibodies and the subject methods will be effective when using a humanized antibody to treat cancer and/or to treat chronic infection.

Example 4

In previous toxicology experiments in cynomolgus monkeys, a single injection of our humanized anti-CD47 monoclonal antibody (Hu5F9-G4) produced unacceptable levels of anemia (Hb>7 g/dL) when dosed at or above 10 mg/kg.

Hu5F9-G4 doses less than 10 mg/kg are insufficient to produce serum levels associated with therapeutic efficacy in our preclinical models (100-200 ug/ml) This new study determined if a single "priming dose" of 5 mg/kg was sufficient to protect cynomologus monkeys from subsequent "maintenance doses" at levels that would otherwise be toxic (and probably lethal) (See study design: FIG. 13).

Figure 14:
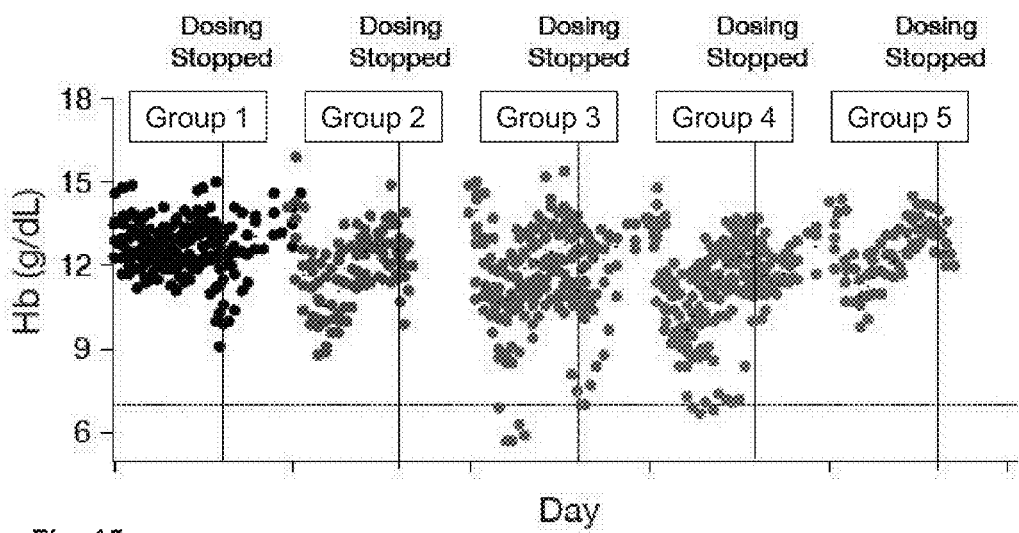
FIG. 14 depicts hemoglobin level data for all cohorts over the duration of the study described in Example 4 (also see FIG. 13).

Despite the anemia related to administration of Hu5F9-G4, no evidence of toxicity was observed in clinical signs in any animal, and thus, the priming/maintenance dosing strategy allows Hu5F9-G4 to be clinically well-tolerated, even at doses as high as 300 mg/kg (FIG. 14). We believe that the administration of Hu5F9-G4 accelerates the process of elimination of aging RBCs by substituting gradual loss of CD47 with immediate blockade of CD47 on aging RBCs. The premature loss of aging RBCs is compensated by an ensuing reticulocytosis (which was observed across all studies), and over time, the initial anemia resolves as the aged RBCs are replaced with younger cells, and as a result, the age distribution of the RBC pool is shifted to younger cells. Serum concentrations in Groups 2-4 (FIG. 13, FIG. 14, FIG. 15) were well above the minimum 100-200 ug/ml level associated with therapeutic efficacy.

FIG. 13. Study design. The animals (# males and females in far right column) were divided into 5 groups, one of which did not receive anti-CD47 antibody. All animals in Groups 2-5 received a priming dose (5 mg/kg) and Groups 2-5 received the listed maintenance doses thereafter.

FIG. 14. Hemoglobin levels in all cohorts over the duration of the study. The horizontal dashed line represents a dose limiting toxicity in this study (Hb<7). Each dot on this graph represents an individual animal. There is no statistical difference in the Hb levels at the different maintenance dose levels. The priming dose (5 mg/kg) protects against subsequent doses no matter how high.

Figure 15:
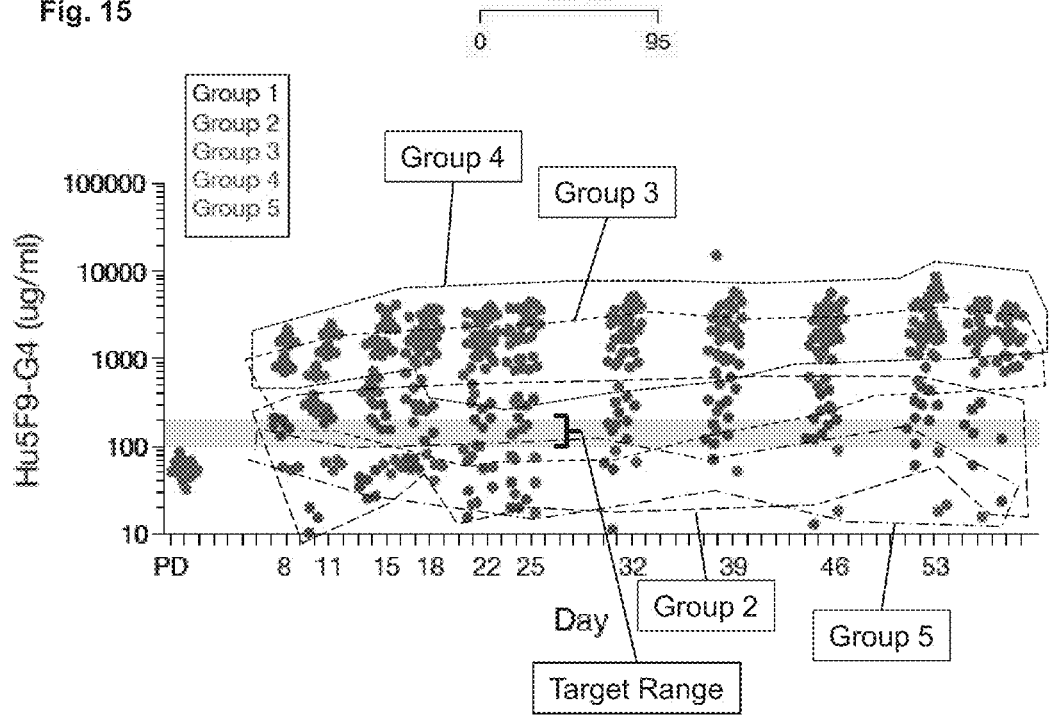
FIG. 15 depicts the pharmacokinetic profile of Hu5F9-G4 (humanized anti-CD47 antibody) in all cohorts of the study described in Example 4 (also see FIG. 13).

FIG. 15. Pharmacokinetic profile of Hu5F9-G4 in all cohorts. Groups 3-4 achieve serum concentrations of Hu5F9-G4 well above minimum concentrations associated with efficacy (Target Range).

Example 5

Studies were conducted in rhesus and/or cynomolgus monkeys, both of which are considered to be pharmacologically relevant animal species (CD47 of rhesus monkeys shares 100% sequence homology with CD47 of cynomolgus monkeys).

All studies were conducted in compliance with United States Food and Drug Administration (FDA) Good Laboratory Practice (GLP) Regulations (21 CFR Part 58). Development of Hu5F9-G4 also followed applicable ICH, Committee on Proprietary, and FDA guidance documents.

In Vitro Hemolysis Assay of Hu5F9-G4 (Humanized Anti-CD47 Antibody)

Because CD47 is expressed on red blood cells and functions in the clearance of aging red blood cells, this study was conducted to evaluate if Hu5F9-G4 caused direct intravascular hemolysis of either human or monkey (rhesus and cynomolgus) red blood cells, using free hemoglobin as a read out. Hu5F9-G4 did not cause hemolysis of either human or monkey (rhesus or cynomolgus) red blood cells.

Cytokine Production in Human PBMC Stimulated with Hu5F9-G4 In Vitro

The objective of this study was to evaluate the potential induction of cytokine release by Hu5F9-G4 in human peripheral blood mononuclear cells (PBMCs). In this in vitro study, cultured PMBCs collected from three separate donors were incubated with either Hu5F9-G4 (20 μg/mL plate bound) or a non-specific human IgG4 antibody (negative control) or anti-CD3/anti-CD28 antibodies (positive control). Fifty different cytokines, including many pro-inflammatory cytokines associated with cytokine storm (e.g., TNF-α, IL-1, IL-4, IL-6) were evaluated by Luminex multiplex analysis. Of the different cytokines evaluated, Hu5F9-G4 did not induce cytokine release in human PBMCs. In addition, no clinical signs of cytokine release syndrome were observed in any of the monkey studies. Treatment of human PBMCs with Hu5F9-G4 did result in a reduction of levels of IL1-RA, MIP1b/CCL4, IL-8, and ENA-78/CXCL5 in comparison to PBMCs treated with the non-specific IgG4 antibody or the CD3/CD28 antibodies. While the relationship between CD47 and these four cytokines is not clear, no evidence of any treatment-related effects that could be directly associated with a reduction in cytokine levels was observed in the monkey studies.

Single Dose Study of Hu5F9-G4 and B6H12-G4 Administered by 1-Hour Intravenous Infusion or Subcutaneous Injection to Cynomolgus Monkeys The purpose of this study was to evaluate the potential toxicity and toxicokinetics of Hu5F9-G4 administered as a single dose by a 1-hour IV infusion to male cynomolgus monkeys. In this study, Hu5F9-G4 was administered at a dose of 10 mg/kg to a single male monkey on Day 1. The monkey was evaluated for changes in clinical signs, food consumption, body weight, and clinical pathology parameters (hematology, coagulation, hematology, clinical chemistry). Samples were collected for toxicokinetic analysis throughout the duration of the study; the animal was returned to the testing facility animal colony on Day 14.

Treatment-related changes were observed in hematology parameters and included mild to moderate decreases in red blood cell count (RBC), hemoglobin, hematocrit, markedly increased reticulocyte counts and red cell distribution width, and transient increases in white blood cell, lymphocyte, and monocyte counts. Changes were also observed in clinical chemistry parameters that were considered likely related to Hu5F9-G4, which included transient increases in lactate dehydrogenase, bilirubin, AST, and ALT. Changes in hematology and clinical chemistry parameters partially or completely returned to baseline levels by Day 14.

In summary, a single administration of Hu5F9-G4 at 10 mg/kg was well tolerated, with treatment-related findings limited to transient changes in hematology and clinical chemistry parameters.

Study Via Intravenous Infusion Administration to Rhesus Monkey

This study was conducted to evaluate the potential effects of Hu5F9-G4 on hematology and clinical chemistry parameters when administered to rhesus monkeys at the same testing facility where the studies in cynomolgus monkeys were conducted (Charles River Laboratories, Reno, Nev.). In this study, Hu5F9-G4 was administered as a single dose to female rhesus monkeys (N=2) via a 1-hour IV infusion at 3 mg/kg. The animals were evaluated for 14 days, and then returned to the facility animal colony.

Administration of HuF59-G4 was well tolerated, and no changes considered directly related to Hu5F9-G4 were noted in clinical signs, body weights, or food consumption. Watery feces were observed in both animals on Days 7, 8, and 14, which was likely related to study-related procedures rather than a direct effect of Hu5F9-G4. In addition, watery feces were not reported in any other monkey study. Treatment-related changes were observed in both animals in hematology parameters, including decreases in RBC and hemoglobin levels; however, these decreases recovered by Day 14 and were not severe with nadirs of 9.4 and 9.1 g/dL (Table 1). Free plasma hemoglobin was not detected in either animal at any time point. An increase in total bilirubin was also observed in each animal, but consistent with the hematology changes, showed a continued trend for reversibility to the end of the study.

In summary, Hu5F9-G4 was well tolerated in rhesus monkeys, and the treatment-related changes observed in this study were consistent with the findings noted in the cynomolgus monkey studies conducted at Charles River Laboratories (Reno, Nev.).

TABLE 1

Changes in Clinical Pathology Parameters in Rhesus Monkeys

| Animal No. | Study Day | RBC ($10^6$/μl) | HGB (g/dL) | Total Bilirubin (mg/dL) |
|---|---|---|---|---|
| 700 | Pre-study | 6.12 | 13.8 | 0.18 |
|  | 1 (8 hr post-dose) | 5.14 | 11.7 | 1.30 |
|  | 1 (24 hr post-dose) | 4.9 | 11.3 | 1.69 |
|  | 2 | 4.36 | 10.0 | 0.98 |
|  | 3 | 4.18 | 9.8 | 0.56 |
|  | 5 | 4.04 | 9.4 | 0.34 |
|  | 7 | 4.11 | 9.9 | 0.49 |
|  | 10 | 4.25 | 10.8 | 0.43 |
|  | 14 | 4.62 | 11.4 | 0.32 |
| 701 | Pre-study | 5.47 | 12.7 | 0.12 |
|  | 1 (8 hr post-dose) | 4.85 | 11.5 | 1.89 |
|  | 1 (24 hr post-dose) | 4.65 | 10.8 | 0.77 |
|  | 2 | 4.21 | 9.9 | 0.44 |
|  | 3 | 4.02 | 9.8 | 0.34 |
|  | 5 | 4.01 | 9.6 | 0.33 |
|  | 7 | 3.89* | 9.1 | 0.41 |
|  | 10 | 4.15 | 10.4 | 0.41 |
|  | 14 | 4.9 | 12.7 | 0.23 |

Pharmacokinetic and Tolerability Study of Hu5F9-G4 Administered to Rhesus Monkeys The initial purpose of this study was to evaluate the pharmacokinetics and potential effects of Hu5F9-G4 administered as a 1-hour IV infusion or by intrathecal administration in rhesus monkeys implanted with an intrathecal reservoir. However, due to the severe anemia observed in the first monkey administered Hu5F9-G4 via a 1-hour IV infusion, the remaining components of the study, including the intrathecal administration phase, were abandoned. In this study, one male rhesus monkey was administered Hu5F9-G4 via a 1-hour IV infusion as a 3 mg/kg priming dose on Day 0, followed by a 1 mg/kg maintenance dose administered on Days 15 and 22 (the maintenance dose in the initial study design was 30 mg/kg administered on Days 8, 15, 22, and 29).

A substantial reduction in RBC counts and hemoglobin was observed within 24 hours following administration of the 3 mg/kg priming dose (Table 2). Due to the anemia observed in this animal, the first scheduled maintenance dose on Day 8 was not administered. The RBC counts and hemoglobin levels showed a trend to recovery, and by Day 14, the RBC counts and hemoglobin levels had return to 4.31 M/μL and 10.8 g/dL, respectively. Dosing was therefore resumed on Day 14; however, the maintenance dose was reduced to 1 mg/kg (rather than 30 mg/kg). On Day 16, the RBC counts and hemoglobin again began to decrease, however, by Day 17, both RBC counts and hemoglobin began to recover. The animal was then administered a second maintenance dose on Day 21 (however, no additional clinical pathology data was collected after Day 21). In addition, while a reduction in platelets was noted two days after administration of the first maintenance dose (on Day 14), the platelets return to pre-study levels by Day 21; it is unclear at this time if the reduction in platelets noted in this animal was directly related to Hu5F9-G4 since this change was not observed in any other monkey studies, including the single dose rhesus monkey study.

TABLE 2

Changes in Hematology Parameters in a Rhesus Monkey Administered Hu5F9-G4

| Study Day | RBC (M/μL) | HGB (g/dL) | Platelets (K/μL) |
|---|---|---|---|
| Pre-study | 5.09 | 12.2 | 548 |
| 0 (8 hr post-dose) | 3.73 | 7.8 | 380 |
| 1 | 3.86 | 8.0 | 411 |
| 2 | 3.42 | 7.2 | 416 |
| 3 | 3.27 | 7.0 | 517 |
| 6 | 3.31 | 7.8 | 661 |
| 9 | 3.56 | 9.1 | 632 |
| 13 | 3.94 | 8.9 | 373 |
| 14 (pre-dose) | 4.31 | 10.8 | 374 |
| 15 | 3.87 | 8.3 | 146 |
| 16 | 3.95 | 8.2 | 130 |
| 17 | 4.19 | 8.5 | 197 |
| 20 | 4.01 | 8.7 | 494 |
| 21 (pre-dose) | 4.37 | 9.1 | 622 |

A Single Dose Study and Repeat Dose Study of Hu5F9-G4 and Single Dose Study of FD6-IgG2 Administered by 1-Hour Intravenous Infusion to Cynomolgus Monkeys The anemia observed in a previous single-dose study may be related to the pharmacological action of Hu5F9-G4 as a result of binding CD47 expressed on RBCs. As RBCs age, they gradually lose CD47 expression, lose sialic acids from glycoproteins and glycolipids, and reorganize membrane phospholipids in a manner that presumably accumulates pro-phagocytic signals, leading to their elimination by phagocytosis (Danon, 1988). We hypothesize that administration of Hu5F9-G4 accelerates the process of aging RBC elimination by substituting gradual loss of CD47 with immediate blockade of CD47 on aging RBCs. The premature loss of aging RBCs is compensated by an ensuing reticulocytosis, and the initial anemia resolves as aged RBCs are replaced with younger RBCs and the age distribution of the RBC pool is shifted to younger cells. Based on these considerations, this study was conducted to assess whether i) initial low doses of Hu5F9-G4 might cause a limited loss of aged RBC that is nevertheless sufficient to induce a reticulocytosis and thereby stimulate production of less-susceptible young RBC and protect the animal from serious anemia; and ii) pre-treatment with Erythropoietin (EPO; an erythropoiesis stimulating agent that stimulates RBC production) may induce production of less-susceptible young RBC, thereby compensating for the clearance of aged RBC following Hu5F9-G4 administration. Another antibody candidate (FD6-IgG2) was evaluated in this study but will not be discussed in this IND. In this study, male cynomolgus monkeys were administered Hu5F9-G4 by a 1-hour IV infusion as a single-dose at 1 mg/kg or once weekly at 3 mg/kg for 4 weeks (Days 1, 8, 15, 22). One monkey administered once weekly doses of Hu5F9-G4 was pre-treated with Erythropoietin (EPO) by IV injection (17,000 U/kg) on Day −5 to assess if pretreatment with EPO would reduce the Hu5F9-G4-related anemia previously observed. In addition, one monkey administered once weekly doses of Hu5F9-G4 was also administered Dexamethasone by IV injection (0.5 mg/kg) and Benadryl by intramuscular (IM)

injection (5 mg/kg) on Days 1, 2, 5, 8, 9, 12, 15, 16, 19, 22, 23, and 26 (Dexamethasone and Benadryl were administered at the same time) to evaluate if administration of Dexamethasone and Benadryl would reduce the Hu5F9-G4-related anemia. The study design is presented in Table 3.

TABLE 3

Single and Repeat Doses of Hu5F9-G4 Administered to Cynomolgus Monkeys

| Group[A] | Hu5F9-G4 Dose (mg/kg) | Hu5F9-G4 Dose Days | Dexamethasone/Benadryl Dose Days[B] | EPO Dose Days[C] |
|---|---|---|---|---|
| 1 | 1 | 1 | — | — |
| 2 | 3 | 1, 8, 15, 22 | 1, 2, 5, 8, 9, 12, 15, 16, 19, 22, 23, 26, | — |
| 3 | 3 | 1, 8, 15, 22 | — | −5 |
| 4 | 3 | 1, 8, 15, 22 | — | — |

[A]Group 1 was released to the animal colony on Day 31; Groups 2 and 4 were terminated on Day 31 and Group 3 was terminated on Day 29
[B]Dexamethasone (IV injection; 0.5 mg/kg) and Benadryl (IM injection; 5 mg/kg) were administered at same time on Days 1, 8, 15, 22 60 minutes prior to Hu5F9-G4
[C]EPO was administered IV at 17,000 U/kg Standard safety parameters (e.g., clinical observations, body weights, clinical pathology, etc.) were incorporated in the study, and because CD47 is expressed in the brain (add reference), veterinary neurologic examinations were performed. Blood was collected at time points across the study for toxicokinetics. Animals in Groups 2 and 3 were terminated on Day 31, and the monkey in Group 4 was terminated on Day 29 (the monkey in Group 1 was returned to the Test Facility animal colony).

No unscheduled deaths occurred and no treatment-related changes were noted in clinical signs, body weights, food consumption, veterinary neurologic examinations, coagulation or urinalysis parameters, organ weights, or macroscopic or microscopic examinations.

Changes related to Hu5F9-G4 were limited to changes in hematology and clinical chemistry parameters. Changes in the single-dose animal (Group 1) included decreased red cell mass (RBC count, hemoglobin, and hematocrit levels) and mean corpuscular volume (MCV), and increased mean corpuscular hemoglobin concentration (MCHC) and red cell distribution width (RDW); these changes were observed by Day 2. This animal also had a robust reticulocyte response, and changes in RBC morphology observed in blood smear evaluations included minimal to mild spherocytes, anisosytosis, and polychromasia. Treatment-related changes in monkeys administered Hu5F9-G4 once weekly included decreases in RBC mass and MCV and increases in MCHC. These changes were noted by Day 3 and were less pronounced in the animal pretreated with EPO compared to the other monkeys administered Hu5F9-G4 alone or with Dexamethasone/Benadryl. The changes in RBC mass partially recovered by Day 27 (5 days after the last dose on Day 22), and were associated with a corresponding robust reticulocytes response. Similar to the single-dose monkey, changes in RBC morphology included minimal to moderate spherocytes, anisosytosis, and polychromasia. Meaningful elevations in free plasma hemoglobin were not detected in the single-dose or repeat-dose Hu5F9-G4-treated monkeys.

Changes in clinical chemistry parameters considered related to Hu5F9-G4 administration included increased lactate dehydrogenase, aspartate aminotransferase (single-dose animal only), total bilirubin (minimal), and decreased haptoglobin (repeat-dose treated Hu5F9-G4 alone and Dexamethasone/Benadryl monkeys only). These changes in clinical chemistry parameters showed evidence of complete or partial recovery by the end of the study.

In summary, administration of Hu5F9-G4 as a single dose at 1 mg/kg or once weekly doses for 4 weeks at a dose of 3 mg/kg (alone or with pretreatment with EPO or in combination with administration of Dexamethasone/Benadryl) was well-tolerated in male cynomolgus monkeys, and treatment related effects were limited to changes in hematology (including RBC morphology) and clinical chemistry parameters. Partial or complete recovery was noted in changes in RBC mass and clinical chemistry parameters by the end of study.

Repeat Dose Study of Hu5F9-G4 or FD6 Monomer, and Single Dose Study of FD6-IgG4 Administered by Intravenous Infusion to Cynomolgus Monkeys Xx The purpose of this study was to evaluate the potential toxicity and toxicokinetics of Hu5F9-G4 when administered to female cynomolgus monkeys via a 1-hour IV infusion at escalating doses over a 5 week period (FD6-IgG2 was another antibody candidate evaluated in this study). In this study, one monkey was administered EPO (17,000 U/kg) on Day −5 followed by escalating doses of Hu5F9-G4 up to 300 mg/kg once weekly on Days 1, 8, 15, 24, and 31; the other monkey was administered escalating doses of Hu5F9-G4 (without pretreatment with EPO) up to 100 mg/kg once weekly on Days 1, 8, 15, 24, and 31. Standard safety parameters were incorporated in this study and both animals were terminated on Day 43 (13 days after the last Hu5F9-G4 dose). The study design is presented in Table 4.

TABLE 4

Escalating Doses of Hu5F9-G4 Administered to Cynomolgus Monkeys

| Group | No. Female Monkeys | Hu5F9-G4 Dose (mg/kg) | Dose Days |
|---|---|---|---|
| 1 (EPO pre-treatment) (17,000 U/mg administered on Day −5) | | 3 | 1 |
| | | 10 | 8 |
| | | 30 | 15 |
| | | 100 | 24 |
| | | 300 | 31 |
| 2 (No EPO) | | 1 | 1 |
| | | 3 | 8 |
| | | 10 | 15 |
| | | 30 | 24 |
| | | 100 | 31 |

Both animals survived to the scheduled end of the study, and no treatment-related changes were noted in clinical signs, body weights, food consumption, coagulation and urinalysis parameters, clinical chemistry parameters indicative of renal, hepatic, or cardiac effect, organ weights, or macroscopic or microscopic examinations. Treatment-related findings were limited to changes in hematology and clinical chemistry parameters. Consistent with previous studies, hematology changes included decreased RBC mass (RBC count, hemoglobin, hematocrit), and increased reticulocyte counts. Other changes included increases in MCHC and RDW and decreases in MCV were also observed. Decreases in RBC count and hemoglobin returned to near prestudy values for both animals by the end of the study (Table 5). A robust reticulocyte count was observed in both animals starting at Day 3, which returned to near prestudy values in both animals by Day 43.

TABLE 5

Changes in Hematology Parameters

| Group/Animal No. | Day | RBC (10^6/μl) | HGB (g/dL) | RETIC (10^5/μl) |
|---|---|---|---|---|
| 1/1501 (EPO Pretreatment) | Prestudy | 5.48 | 13.0 | 0.66 |
| | 3 | 4.39 | 10.7 | 6.8 |
| | 5 | 4.43 | 10.7 | 5.32 |
| | 13 | 4.28 | 10.8 | 3.0 |
| | 20 | 4.25 | 10.8 | 3.61 |
| | 30 | 4.64 | 11.6 | 2.32 |
| | 43 | 4.98 | 12.3 | 1.54 |
| 2/2501 (No EPO) | Prestudy | 5.3 | 12.1 | 0.53 |
| | 3 | 4.19 | 9.6 | 3.27 |
| | 5 | 4.47 | 10.3 | 5.86 |
| | 13 | 4.6 | 11.5 | 5.93 |
| | 20 | 4.76 | 11.4 | 4.43 |
| | 30 | 4.76 | 12.7 | 2.77 |
| | 43 | 5.74 | 13.2 | 0.80 |

Changes in RBC morphology were consistent with previous studies and included minimal to marked microcytes, anisocytosis, polychromasia, and spherocytosis. As expected (based on the pharmacological action of EPO) these changes were more pronounced in Animal No. 2501 (no EPO pretreatment) compared to Animal No. 1501. Changes in RBC morphology showed partial or complete recovery by Day 37 (Table 6).

TABLE 6

Red Blood Cell Morphologies

| Group/Animal No. | Study Day | Aniso-cytosis | Microcytes | Polychromasia | Spherocytes |
|---|---|---|---|---|---|
| 1/1501 (EPO Pretreatment) | 3 | 1+ | — | 2+ | 2+ |
| | 5 | 1+ | — | 2+ | 1+ |
| 2/2501 (No EPO) | 3 | 1+ | — | 1+ | 3+ |
| | 5 | 1+ | — | 2+ | 1+ |
| | 10 | 1+ | 3+ | 2+ | 4+ |
| | 13 | 3+ | 2+ | 1+ | 2+ |
| | 17 | 1+ | — | 2+ | 1+ |
| | 20 | 3+ | 2+ | 1+ | — |
| | 37 | 1+ | — | — | — |

1+ = minimal;
2+ = mild;
3+ = moderate;
4+ = marked;
— = not applicable

In addition, increased lymphocyte, and monocyte counts were observed in both animals, which were highest around Day 20 and ranged from 2.58-3.7-fold above prestudy values for lymphocytes and 4.4-6.13-fold above prestudy values for monocyte counts. Clinical chemistry changes included decreased haptoglobin observed in both animals, which returned to prestudy levels by the end of the study. Increased bilirubin was also observed on Day 13 for Animal No. 2501 (no EPO pretreatment).

Toxicokinetics confirmed exposure to Hu5F9-G4 in both animals, and circulating concentrations of Hu5F9-G4 generally increased as the dose increased. Administration of Hu5F9-G4 at doses up to 100 mg/kg resulted in a median half-life of 14 hours.

In summary, administration of escalating doses of Hu5F9-G4 administered by a 1-hour IV infusion once weekly at doses up to 100 mg/kg (no EPO pretreatment) or 300 mg/kg (EPO pretreatment) was generally well-tolerated by cynomolgus monkeys. Treatment-related changes were limited to hematology (including RBC morphology) and clinical chemistry parameters, which were partially or completely reversible by the end of the study.

A Single or Escalating Dose Study of Hu5F9-G4 Administered by 1-Hour Intravenous Infusion to Female Cynomolgus Monkeys Based on the previous study, initial administration of Hu5F9-G4 at lower doses enables subsequent administration of higher doses that are tolerated in cynomolgus monkeys. The purpose of this study was to evaluate the potential toxicity and toxicokinetics of Hu5F9-G4 when administered as a priming dose at a low dose level followed by multiple maintenance doses at higher dose levels. In addition, this study was designed to model the potential clinical dosing schedule using a priming/maintenance-dosing regimen. In this study, female cynomolgus monkeys were administered phosphate buffered saline (PBS) or escalating doses of Hu5F9-G4 (ranging from 0.1 to 30 mg/kg) by a 1-hour IV infusion as a single priming dose on Day 1 (Groups A and H). Animals in Groups B-F were administered PBS or Hu5F9-G4 as a priming dose on Day 1, followed by multiple maintenance doses of PBS or various dose levels of Hu5F9-G4. One animal in Group D (10501) and Group F (12501) was administered a second priming/maintenance dose cycle starting on Day 68 (priming dose of 3 mg/kg) followed by twice weekly maintenance doses (30 mg/kg) for 2 weeks on Days 75, 78, 82, and 85. While the first priming dose on Day 1 for Animal No. 10501 was 1 mg/kg, the second priming dose on Day 68 was increased to 3 mg/kg to evaluate if this increase in priming dose level would be tolerated (the priming dose on Days 1 and 68 for Animal No. 12501 was 3 mg/kg). Rather than having a priming/maintenance dose schedule, the animal in Group G was administered Hu5F9-G4 once weekly at 10 mg/kg on Days 1, 8, 15, and 22 (due to low RBC mass, the Day 15 dose was not administered). The study design is presented in Table 7.

TABLE 7

Administration of Hu5F9-G4 as a Priming/Maintenance Dose Schedule to Cynomolgus Monkeys

| Animal No. | Group | No. of Test Animals | Material | Dose Day(s)^A | Dose Level (mg/kg) |
|---|---|---|---|---|---|
| 1501 | A | 1 | PBS | 1 | 0 |
| 2501 | A | 1 | Hu5F9-G4 | 1 | 0.1 |
| 3501 | A | 1 | Hu5F9-G4 | 1 | 0.3 |
| 4501 | A | 1 | Hu5F9-G4 | 1 | 1 |
| 5501 | A | 1 | Hu5F9-G4 | 1 | 3 |
| 6501 | A | 1 | Hu5F9-G4 | 1 | 10 |
| 7501 | A | 1 | Hu5F9-G4 | 1 | 30 |
| 8501 | B | 1 | PBS | 1 | 0 |
| | | | | 8 | |
| | | | | 15 | |
| | | | | 22 | |
| | | | | 29 | |
| | | | | 36 | |
| | | | | 43 | |
| | | | | 68 | |
| | | | | 75 | |
| | | | | 78 | |
| | | | | 82 | |
| | | | | 85 | |
| 9501 9502 | C | 2 | Hu5F9-G4 | 1 | 1 |
| | | | | 8 | 10 |
| | | | | 15 | |
| | | | | 22 | 10 |
| | | | | 29 | 10 |
| | | | | 36 | 10 |
| | | | | 43 | 10 |

TABLE 7-continued

Administration of Hu5F9-G4 as a Priming/Maintenance Dose Schedule to Cynomolgus Monkeys

| Animal No. | Group | No. of Test Animals | Material | Dose Day(s)[A] | Dose Level (mg/kg) |
|---|---|---|---|---|---|
| 10501[D] | D | 2 | Hu5F9-G4 | 1 | 1 |
| 10502 | | | | 8 | 30 |
| | | | | 15 | |
| | | | | 22 | |
| | | | | 29 | 30 |
| | | | | 36 | 30 |
| | | | | 43 | 30 |
| | | | | 68[B] | 3 |
| | | | | 75[B] | 30 |
| | | | | 78[B] | 30 |
| | | | | 82[B] | 30 |
| | | | | 85[B] | 30 |
| 11501 11502 | E | 2 | Hu5F9-G4 | 1 | 3 |
| | | | | 8 | 10 |
| | | | | 15 | |
| | | | | 22 | |
| | | | | 29 | 10 |
| | | | | 36 | 10 |
| | | | | 43 | 10 |
| 12501[D] 12502 | F | 2 | Hu5F9-G4 | 1 | 3 |
| | | | | 8 | 30 |
| | | | | 15 | |
| | | | | 22 | |
| | | | | 29 | 30 |
| | | | | 36 | 30 |
| | | | | 43 | 30 |
| | | | | 68[B] | 3 |
| | | | | 75[B] | 30 |
| | | | | 78[B] | 30 |
| | | | | 82[B] | 30 |
| | | | | 85[B] | 30 |
| 13501 | G | 1 | Hu5F9-G4 | 1 | 10 |
| | | | | 8 | |
| | | | | 15[C] | |
| | | | | 22 | |
| 14401 | H | 1 | Hu5F9-G4 | 1 | 30 |

[A]Priming dose administered on Day 1; maintenance doses administered on all subsequent days.
[B]Dosing on Days 68 (priming dose) followed by maintenance doses on Days 75, 78, 82, and 85 applicable to only 1 animal in this group (Animal 10501 in Group D and Animal 12501 in Group F).
[C]Animal had a dose holiday on this day due to low RBC mass
[D]Animal Nos. 10501 and 12501 were terminated on Day 120 and subjected to full necropsy; all other animals were returned to the Facility's animal colony on Day 120.

All animals were evaluated for changes in clinical signs, food consumption, body weights, clinical pathology parameters (hematology, coagulation, clinical chemistry, urinalysis). Blood samples were collected throughout the study for toxicokinetics and evaluation of ADA responses. Due to the level of decreased RBC mass, a dose holiday occurred on Day 15 for the animal in Group G (13501; priming/maintenance dose of 10 mg/kg); this animal was administered the last scheduled dose on Day 22. Animals were returned to the Testing Facility colony on Day 120, except for Animal Nos. 10501 (Group D) and 12501 (Group F) that were euthanized on Day 120, and subjected to a full necropsy examination; organ weights and microscopic examination of tissues were also performed.

No unscheduled deaths occurred, and overall administration of Hu5F9-G4 was clinically well tolerated. Findings considered related to Hu5F9-G4 were limited to changes in hematology and clinical chemistry parameters.

Single-Dose Groups (A and H): Hematology Parameters

Hematology changes were noted in animals administered a single dose of Hu5F9-G4 (Groups A and H). Variable decreases in RBC mass were observed in animals in Group A (administered escalating priming doses ranging from 0.1 to 30 mg/kg) during Days 3 to 14 in dose groups ≥0.3 mg/kg (no changes were observed for 0.1 mg/kg). The decreases in RBC mass ranged up to 0.73-fold below prestudy levels for 0.3 mg/kg, 0.63-fold below prestudy for 1 and 10 mg/kg, and 0.53-fold below prestudy for 30 mg/kg (Table 8). Interestingly, the RBC mass for the animal in Group H decreased only slightly below prestudy levels even though this animal was administered the highest priming dose (30 mg/kg). These decreases, however, showed a continued trend to recovery to the last time point evaluated for Groups A and H. Reticulocyte counts increased for all animals (including control), indicating responsive erythropoiesis. In addition, increases in MCHC (≥0.3 mg/kg) and RDW 0.1 mg/kg) were noted, with increases up to 1.2-fold above prestudy values for MCHC and 2-fold above prestudy values for RDW. Decreases in MCV were also noted at doses 0.3 mg/kg, which ranged up to 0.91-fold below prestudy values. Free plasma hemoglobin was not detected in any animal. Lymphocyte counts increased at doses ≥0.3 mg/kg, with values ranging from 1.19- to 1.86-fold above prestudy values; increases in lymphocytes corresponded with white blood cell counts, which ranged up to 2.5-fold above prestudy. Changes in RBC morphologies were evaluated on Days 6 and 10, and noted at doses ≥0.1 mg/kg; these changes increased in severity with higher doses (0.3 to 30 mg/kg) and included minimal to marked macrocytes, microcytes, anisocytosis, polychromasia, and spherocytosis.

TABLE 8

Changes in Hematology Parameters for Animals Administered a Single Priming Dose of Hu5F9-G4 (Groups A and H)

| Animal No. (dose of Hu5F9-G4) | Study Day | RBC ($10^6/\mu l$) | HGB (g/dL) |
|---|---|---|---|
| Group A | | | |
| 1501 (control) | Pre-study | 5.87 | 13.5 |
| | 3 | 5.46 | 12.6 |
| | 6 | 5.20 | 12.0 |
| | 14 | 5.63 | 13.0 |
| | 42 | 5.55 | 13.1 |
| 2501 (0.1 mg/kg) | Pre-study | 5.62 | 13.9 |
| | 3 | 5.07 | 12.5 |
| | 6 | 4.67 | 11.6 |
| | 14 | 5.27 | 13.1 |
| | 42 | 5.82 | 14.4 |
| 3501 (0.3 mg/kg) | Pre-study | 5.58 | 12.8 |
| | 3 | 4.92 | 11.2 |
| | 6 | 4.44 | 10.4 |
| | 14 | 5.20 | 12.1 |
| | 42 | 5.88 | 13.5 |
| 4501 (1 mg/kg) | Pre-study | 5.31 | 13.8 |
| | 3 | 3.75 | 9.7 |
| | 6 | 3.65 | 9.6 |
| | 14 | 4.39 | 11.5 |
| | 42 | 5.51 | 14.3 |
| 5501 (3 mg/kg) | Pre-study | 5.64 | 13.0 |
| | 3 | 4.68 | 11.0 |
| | 6 | 4.05 | 9.9 |
| | 14 | 4.44 | 11.6 |
| | 42 | 5.56 | 13.8 |
| 6501 (10 mg/kg) | Pre-study | 6.24 | 14.2 |
| | 3 | 5.01 | 11.2 |
| | 6 | 4.14 | 9.7 |
| | 14 | 5.24 | 12.1 |
| | 42 | 6.25 | 14.4 |
| 7501 (30 mg/kg) | Pre-study | 5.22 | 12.5 |
| | 3 | 4.69 | 11.2 |
| | 6 | 3.02 | 7.3 |
| | 14 | 3.98 | 9.9 |
| | 42 | 5.37 | 12.8 |

TABLE 8-continued

Changes in Hematology Parameters for Animals Administered a Single Priming Dose of Hu5F9-G4 (Groups A and H)

| Animal No. (dose of Hu5F9-G4) | Study Day | RBC ($10^6/\mu l$) | HGB (g/dL) |
|---|---|---|---|
| Group H | | | |
| 14501 (30 mg/kg) | Pre-study | 5.99 | 13.9 |
| | 3 | 4.9 | 11.2 |
| | 6 | 4.76 | 11.3 |
| | 14 | 4.87 | 11.8 |
| | 42 | 5.77 | 14.0 |

Priming/Maintenance Groups (B-F) and Once Weekly Dosing (Group G): Hematology Parameters Hematology changes observed in animals administered a priming dose on Day 1 followed by repeat maintenance doses of Hu5F9-G4 (Groups B-F) and HuF59-G4 once weekly (Group G) were consistent with those observed in single-dose animals (Groups A and H). Variable decreases in RBC mass (RBC counts, hemoglobin, hematocrit) were observed in Groups administered priming doses ≥1 mg/kg and maintenance doses ≥10 mg/kg (Tables 9-10). These decreases in RBC mass tended to be greater at earlier time points (Days 5, 8 12). In addition, the decreases in RBC mass were greater for the animal administered 10 mg/kg once weekly (Animal No. 13501; Group G) compared to the other animals administered the priming/maintenance dose schedule. Interestingly, while the hemoglobin levels for Animal No. 10501 (Group D) decreased following the first priming dose of 1 mg/kg on Day 1, hemoglobin levels did not drop following the second higher priming dose on Day 68 or after the second cycle of maintenance doses on Days 75, 78, 82, and 85 (Tables 9-10). Additionally, the hemoglobin level for the other animal (No. 12501; Group F) administered a second priming/maintenance cycle remained at prestudy levels during the second cycle. These data indicate that the anemia produced by priming doses below 10 mg/kg is less severe compared to priming doses ≥10 mg/kg, and the lower priming doses allow continued maintenance dosing of Hu5F9-G4 that is tolerated by cynomolgus monkeys. Further, these data show that the priming/maintenance-dosing schedule does not produce an anemia as severe as that observed with the once weekly dose schedule (Group G). For all priming/maintenance groups, there was a trend to recovery in RBC mass to the end of the study. Animal 13501 (Group G, 10 mg/kg once weekly) had a dose holiday on Day 15 due to low RBC mass (hemoglobin level was 6.5 g/dL on Day 12). Hemoglobin levels, however, began to recover on Day 19, and thus, dosing resumed for this animal, which was administered the last dose on Day 22 (Tables 9-10). The hemoglobin levels for Animal No. 13501 steadily maintained a trend towards recovery, and by the last time point (Day 71), returned to slightly above prestudy levels. Reticulocyte counts were increased for all Groups (B-F, including the control group), which indicate responsive erythropoiesis. The MCHC and RDW variably increased at priming/maintenance doses ≥1/10 mg/kg with values ranging up to 1.21-fold above prestudy for MCHC and 2.41-fold above prestudy for RDW. Variable decreases (up to 0.90-fold above prestudy) in MCV were also observed. Similar to the changes in RBC mass, the changes observed in MCHC, RDW, and MCV were more pronounced in Animal No. 13501 (Group G) administered 10 mg/kg once weekly compared to the other animals administered the priming/maintenance dose schedule. Changes in MCHC, RDW, and MCV showed a continued trend for recovery to or near prestudy levels, indicating these changes were reversible. Importantly, free plasma hemoglobin was not observed in any animal. Changes in RBC morphology (consistent with changes in hematology parameters) were also observed, and included anisocytosis, macrocytes, microcytes (not observed at priming/maintenance dose of 3/30 mg/kg), polychromasia, and spherocytes. Overall, the incidence and severity of these changes did not occur in a dose-dependent manner, and based on the time points evaluated, showed a trend to partial or complete recovery by the end of the study. Lymphocyte counts also increased at priming/maintenance doses ≥1/10 mg/kg, ranging from 1.25- to 2.01-fold above prestudy values, and consistent with other parameters, overall showed a trend for recovery.

TABLE 9

Changes in Hematology Parameters for Animals Administered Priming/Maintenance Dosing (Groups B-F)

| Animal No. (priming/maintenance dose) | Study Day | RBC ($10^6/\mu l$) | HGB (g/dL) | RETIC ($10^9/L$) |
|---|---|---|---|---|
| Group B | | | | |
| 8501 (control) | Pre-study | 6.01 | 14.1 | 102.2 |
| | 5 | 5.31 | 12.7 | 98.7 |
| | 12 | 5.55 | 13.1 | 169.0 |
| | 22 | 5.35 | 12.6 | 228.8 |
| | 43 | 5.54 | 13.0 | 181.5 |
| | 64 | 5.65 | 13.5 | 155.1 |
| Group C | | | | |
| 9502 (1/10 mg/kg) | Pre-study | 5.73 | 13.3 | 51.8 |
| | 5 | 4.08 | 9.8 | 337.7 |
| | 12 | 3.18 | 8.4 | 438.2 |
| | 22 | 3.88 | 10.5 | 602.9 |
| | 43 | 5.05 | 12.3 | 92.6 |
| | 64 | 5.40 | 13.0 | 54.8 |
| Group D | | | | |
| 10501 (1 and 3/30 mg/kg) | Pre-study | 5.53 | 13.5 | 42.2 |
| | 5 | 3.91 | 9.9 | 239.0 |
| | 12 | 3.18 | 8.8 | 479.1 |
| | 22 | 4.11 | 11.5 | 395.5 |
| | 42 | 4.39 | 11.7 | 317.4 |
| | 64 | 4.86 | 12.8 | 143.3 |
| | 68 | 5.03 | 13.2 | 158.9 |
| | 78 | 4.61 | 12.2 | 290.7 |
| | 88 | 4.37 | 12.0 | 362.8 |
| | 106 | 4.62 | 12.1 | 336.5 |
| 10502 (1/30 mg/kg) | Pre-study | 5.95 | 13.6 | 44.1 |
| | 5 | 4.44 | 10.0 | 195.2 |
| | 12 | 4.09 | 9.3 | 246.3 |
| | 22 | 3.86 | 9.7 | 683.2 |
| | 42 | 5.12 | 11.9 | 169.8 |
| | 64 | 5.60 | 13.0 | 122.5 |
| Group E | | | | |
| 11501 (1/10 mg/kg) | Pre-study | 5.36 | 12.0 | 50.9 |
| | 5 | 3.80 | 8.5 | 171.9 |
| | 12 | 3.84 | 8.8 | 381.8 |
| | 22 | 4.69 | 10.8 | 314.5 |
| | 42 | 5.17 | 11.2 | 115.3 |
| | 64 | 5.37 | 11.9 | 56.2 |
| 11502 (1/10 mg/kg) | Pre-study | 5.85 | 14.2 | 94.4 |
| | 5 | 4.42 | 10.8 | 234.0 |
| | 12 | 4.21 | 10.7 | 812.8 |
| | 22 | 4.77 | 11.8 | 497.6 |
| | 42 | 5.02 | 11.8 | 157.7 |
| | 64 | 5.84 | 14.2 | 127.3 |
| Group F | | | | |
| 12501 (3 and 3/30 mg/kg) | Pre-study | 5.54 | 13.0 | 61.9 |
| | 5 | 4.46 | 10.7 | 202.6 |
| | 12 | 4.32 | 10.8 | 330.0 |
| | 22 | 4.97 | 11.6 | 212.3 |

TABLE 9-continued

Changes in Hematology Parameters for Animals Administered Priming/Maintenance Dosing (Groups B-F)

| Animal No. (priming/maintenance dose) | Study Day | RBC ($10^6$/μl) | HGB (g/dL) | RETIC ($10^9$/L) |
|---|---|---|---|---|
| | 42 | 4.72 | 11.5 | 151.5 |
| | 64 | 5.33 | 12.8 | 135.0 |
| | 68 | 5.75 | 13.5 | 112.0 |
| | 78 | 5.30 | 12.9 | 134.3 |
| | 88 | 5.03 | 12.3 | 164.1 |
| | 106 | 5.40 | 13.1 | 174.1 |
| 12502 (3/30 mg/kg) | Pre-study | 5.26 | 12.6 | 62.9 |
| | 5 | 4.09 | 10.0 | 181.3 |
| | 12 | 4.07 | 10.1 | 222.2 |
| | 22 | 4.53 | 11.1 | 275.7 |
| | 42 | 4.75 | 11.2 | 196.2 |
| | 64 | 5.04 | 12.6 | 115.0 |

TABLE 10

Changes in Hematology Parameters for Animal No. 13501 (Group G) Administered 10 mg/kg Hu5F9-G4 Once Weekly

| Group/Animal No. | Study Day | RBC ($10^6$/μl) | HGB (g/dL) | RETIC ($10^9$/L) |
|---|---|---|---|---|
| Group G/13501[A] | Pre-study | | | |
| | 5 | 3.70 | 8.6 | 217.6 |
| | 12 | 2.73 | 6.5 | 196.3 |
| | 19 | 3.63 | 9.1 | 312.7 |
| | 22 | 4.19 | 10.3 | 230.1 |
| | 40 | 5.48 | 13.1 | 101.3 |
| | 50 | 5.37 | 12.8 | 82.1 |
| | 71 | 6.01 | 13.8 | 75.8 |

[A]A dose holiday occurred on Day 15

Single-Dose Groups (A and H): Clinical Chemistry Parameters

In single dose animals (Groups A and H), increase in total bilirubin was noted at doses ≥1 mg/kg, with the increases occurring on Day 6 and ranged from 1.56- to 3.29-fold above prestudy values; increases in total bilirubin did not occur in a dose-dependent manner and showed a trend to recovery. An increase in ALT and AST was noted in a single animal administered 30 mg/kg (Animal 14501; Group H) on Day 6, but these increases showed a trend to recovery by the last time point. Haptoglobin decreased at doses 0.1 mg/kg, however, haptoglobin was below detection levels at 3 to 4 time points for all animals, including prestudy for two Hu5F9-G4-treated animals and one PBS control animal on Day 42. Thus, the decreases in haptoglobin were considered to have an uncertain relationship to single dose administration of Hu5F9-G4 in this study.

Priming/Maintenance Groups (B-F) and Once Weekly Dosing (Group G): Clinical Chemistry Parameters Similar to the single dose groups, total bilirubin was increased in all groups administered the priming/maintenance dose schedule; levels in total bilirubin, however, remained below 1 mg/dL throughout the study (Table 11). Increases in total bilirubin showed a trend to recover at the end of the study. Haptoglobin levels decreased for all groups, which showed a trend to recover at the end of the study (Table 11). Sporadic changes in ALT, AST, and LDH occurred in a couple of animals at some time points during the course of the study; however, these changes, were within normal limits (based on the Test Facility's historical database), occurred on only 1 or 2 days during the study period, and were transient in nature.

TABLE 11

Priming/Maintenance (Groups B-F) and Once Weekly Dosing (Group G): Clinical Chemistry Parameters

| Group/Animal No. (dose) | Study Day | Total Bili (mg/dL) | HAPTO (g/L) |
|---|---|---|---|
| Group B | | | |
| 8501 (control) | Pre-study | 0.23 | 0.48 |
| | 5 | 0.31 | 0.46 |
| | 12 | 0.23 | 0.92 |
| | 26 | 0.22 | 0.70 |
| | 40 | 0.21 | 0.66 |
| | 78 | 0.13 | 0.61 |
| Group C | | | |
| 9502 (1/10 mg/kg) | Pre-study | 0.17 | 0.30 |
| | 5 | 0.28 | 0.15 |
| | 12 | 0.72 | 0.15 |
| | 26 | 0.20 | 0.15 |
| | 57 | 0.18 | 0.34 |
| Group D | | | |
| 10501 (1 and 3/30 mg/kg) | Pre-study | 0.28 | 0.40 |
| | 5 | 0.25 | 0.15 |
| | 12 | 0.53 | 0.15 |
| | 26 | 0.35 | 0.15 |
| | 47 | 0.32 | 0.15 |
| | 68 | 0.21 | 0.15 |
| | 106 | 0.38 | 0.15 |
| 10502 (1/30 mg/kg) | Pre-study | 0.22 | 0.95 |
| | 5 | 0.22 | 0.94 |
| | 12 | 0.34 | 0.15 |
| | 26 | 0.21 | 0.15 |
| | 57 | 0.16 | 0.41 |
| | 5 | 0.22 | 0.94 |
| Group E | | | |
| 11501 (1/10 mg/kg) | Pre-study | 0.23 | 0.36 |
| | 5 | 0.28 | 0.34 |
| | 26 | 0.22 | 0.55 |
| | 40 | 0.17 | 0.69 |
| | 57 | 0.22 | 0.41 |
| 11502 (1/10 mg/kg) | Pre-study | 0.12 | 0.61 |
| | 5 | 0.18 | 0.15 |
| | 12 | 0.33 | 0.15 |
| | 26 | 0.20 | 0.44 |
| | 40 | 0.13 | 1.81 |
| | 57 | 0.12 | 0.60 |
| Group F | | | |
| 12501 (3 and 3/30 mg/kg) | Pre-study | 0.39 | 0.35 |
| | 5 | 0.38 | 0.30 |
| | 12 | 0.52 | 0.15 |
| | 26 | 0.27 | 0.15 |
| | 47 | 0.25 | 0.33 |
| | 68 | 0.25 | 0.15 |
| | 106 | 0.34 | 0.15 |
| 12502 (3/30 mg/kg) | Pre-study | 0.20 | 0.32 |
| | 5 | 0.39 | 0.31 |
| | 12 | 0.54 | 0.34 |
| | 26 | 0.37 | 0.15 |
| | 40 | 0.29 | 0.34 |
| | 57 | 0.25 | 0.15 |
| Group G | | | |
| 13501 (10 mg/kg once weekly) | Pre-study | 0.15 | 0.90 |
| | 5 | 0.56 | 0.15 |
| | 26 | 0.19 | 0.61 |
| | 40 | 0.12 | 0.73 |
| | 71 | 0.12 | 0.79 |

Animal Nos. 10501 (Group D) and 12501 (Group F) were euthanized on Day 120, and subjected to a full necropsy examination; organ weights and microscopic examination of tissues were also performed. While a single, minimal focus of white matter degeneration characterized by axonal degeneration with phagocytes and mononuclear cell infiltrates was noted within the medulla oblongata of Animal No. 10501, it is unknown if this finding was incidental or related to Hu5F9-G4 due to the minimal nature of the finding and the small number (2) of animals subjected to microscopic examination. Importantly, this finding was not noted in the pivotal GLP 8-week toxicology study, which indicates that this finding was likely incidental in nature.

Toxicokinetics showed that no measurable concentrations of Hu5F9-G4 were obtained for Groups administered a single dose of Hu5F9-G4 at doses ≤0.3 mg/kg. $C_{max}$ and $AUC_{0-t}$ generally increased as the dose increased, and increases in $C_{max}$ appeared to be greater than dose proportional for doses ≥1 mg/kg. Increases in $AUC_{0-t}$ were also not proportional with dose. The $T_{1/2}$ for the 10 and 30 mg/kg dose levels were 10.7 to 46.5 hours, respectively, and suggests $T_{1/2}$ may increase with an increase in dose.

For groups administered repeat doses, following a priming dose of 1 or 3 mg/kg (on Day 1 or 68) and repeat administration of 10 or 30 mg/kg, mean $C_{max}$ increased from Day 1 to Day 8; this increase in $C_{max}$ was greater than dose proportional from Day 1 to Day 8. Following a priming dose of 1 (Day 1) or 3 (Day 68) mg/kg and maintenance dosing of 30 mg/kg, mean $C_{max}$ increased from Day 1 to Day 8; this increase in $C_{max}$ was greater than dose proportional from Day 1 to Day 8. Half-life ranged from 10.8 to 173 hours. Some animals had lower than expected serum concentrations of Hu5F9-G4, which suggests the presence of ADA.

In summary, administration of Hu5F9-G4 as a single priming dose up to 30 mg/kg or as a priming/maintenance dose of up to 3/30 mg/kg for up to 2 priming/maintenance dose schedules was clinically well tolerated in cynomolgus monkeys. While once weekly administration of Hu5F9-G4 at 10 mg/kg was clinically well tolerated, a dose holiday was necessary on Day 15 due to the low RBC mass; however, the hemoglobin level showed a trend for recovery on Day 19, and thus, dosing resumed for this animal. Treatment-related changes were limited to alterations in hematology (including RBC morphology) and clinical chemistry parameters. Decreases in RBC mass were consistent with previous studies, and the decreases in RBC count and hemoglobin are likely associated with the postulated pharmacological action of Hu5F9-G4 by binding to CD47 on aged RBCs and accelerating their clearance. It is believed that this clearance of aged RBCs results in the initial anemia and compensating reticulocytosis observed at early time points to replace the aged RBCs with younger RBCs. All of the treatment-related changes in hematology and clinical chemistry parameters showed trends for partial or complete recovery by the end of the study, indicating that these effects of Hu5F9-G4 are reversible. Importantly, the data demonstrate that the anemia induced by the priming/maintenance dose schedule is not as severe as with once weekly dosing, and priming doses ≤10 mg/kg are better tolerated. As such, the priming/dose schedule, with a priming dose ≤10 mg/kg was used in subsequent studies.

Pharmacokinetics of Hu5F9-G4 Following Intravenous Infusion Administration to Cynomolgus Monkeys The purpose of this study was to evaluate the potential toxicity and toxicokinetics of Hu5F9-G4 when administered by a 1-hour IV infusion as a priming/maintenance dose schedule at dose levels not evaluated in previous studies. In this study, Hu5F9-G4 was administered to male cynomolgus monkeys as a priming dose at 5 mg/kg on Day 1, followed by twice weekly maintenance doses at 150 mg/kg on Days 8, 11, 15, 18, 22, and 25. The study design is presented in Table 12.

TABLE 12

Priming/Mainte Priming and Maintenance Dosing of Hu5F9-G4 in Cynomolgus Monkeys

| Group | No. Male Monkeys | Hu5F9-G4 Priming Dose (mg/kg) | Dose Day Priming Dose | Hu5F9-G4 Maintenance Dose (mg/kg) | Dose Days Maintenance Dose |
|---|---|---|---|---|---|
| 1 | 2 | 5 | 1 | 150 | 8, 11, 15, 18, 22, 25 |

The animals were evaluated for changes in clinical signs, body weight, hematology, coagulation, and clinical chemistry parameters (collected up to Day 77); blood samples were also collected to evaluate receptor occupancy using flow cytometry, however, the data is not presented in this IND. Samples were collected throughout the study up to Day 149 for toxicokinetics and assessment of ADA responses. Both animals were returned to the Test Facility animal colony at the end of the study.

Both animals survived to the scheduled end of the study, and no evidence of treatment-related effects was noted in clinical signs, food consumption, or body weight. Treatment-related findings were observed in both animals and included changes in hematology and clinical chemistry parameters. Consistent with previous studies, mild anemia was noted in both animals on Day 5 (4 days after the 5 mg/kg priming dose). A significant reduction in RBC count was observed in both animals beginning on Day 8 (Animal 1036) and Day 11 (Animal 1037). On Day 18, a trend for the RBC returning to normal levels was observed in Animal 1036; however, Animal 1037 continued to show significant reductions in RBC count (Table 13). The reduction in RBC count coincided with a significant increase in reticulocytes for both animals (Table 13). Similar to the RBC count, a trend for reticulocytes returning to normal levels was observed for Animal 1036; however, reticulocytes continued to increase for Animal 1037. In addition, hemoglobin levels were significantly reduced in Animal 1037 (starting on Day 15). The hemoglobin levels for Animal 1036 also decreased, however, the decrease observed in this animal was not as significant as Animal 1037, and remained above 10.0 g/dL during the study except on Day 11 where the hemoglobin dropped slightly below 10.0 g/dL (Table 13). Free plasma hemoglobin was not observed in either animal. Dosing was stopped on Day 15 for Animal 1037 due to the severe anemia. Dosing was not resumed for this animal to assess if the anemia would recover; thus, Animal No. 1037 was not dosed on Days 18, 22, and 25. Since the hemoglobin levels for Animal 1036 remained above 10.0 g/dL throughout the majority of the study, dosing continued as planned. Despite the anemia, no clinical signs indicative of toxicity were observed in either animal. In addition, no major changes in other clinical pathology parameters were observed, including white blood cell counts, platelets, or creatinine levels. Both animals were examined by a staff veterinarian on Day 22 with special attention to palpation of the spleen; palpation of the spleen revealed no abnormalities in either animal.

TABLE 13

Changes in Hematology Parameters

| Animal No. | Study Day | RBC ($10^6$/μl) | HGB (g/dL) | RETIC ($10^9$/L) |
|---|---|---|---|---|
| 1036 | Prestudy | 5.87 | 13.8 | 75.4 |
|  | 5 | 4.24 | 10.4 | 234.6 |
|  | 8 | 3.92* | 10.0 | 984.3 |

TABLE 13-continued

Changes in Hematology Parameters

| Animal No. | Study Day | RBC (10^-6/μl) | HGB (g/dL) | RETIC (10^9/L) |
|---|---|---|---|---|
| | 11 | 3.75* | 9.8 | 847.7 |
| | 15 | 3.94* | 10.3 | 557.5 |
| | 18 | 4.3 | 10.8 | 542.1 |
| | 22 | 4.45 | 11.6 | 414.5 |
| | 25 | 4.51 | 11.5 | 329.4 |
| | 29 | 4.59 | 11.7 | 374.2 |
| | 48 | 5.07 | 12.9 | 236.1 |
| | 77 | 5.25 | 13.5 | 258.6 |
| 1037 | Prestudy | 6.47 | 14.3 | 51.4 |
| | 5 | 4.85 | 11.1 | 232 |
| | 8 | 4.13 | 10.0 | 937.1 |
| | 11 | 3.24* | 8.0 | 612.9 |
| | 15 | 2.23* | 5.5* | 670.3 |
| | 18 | 1.86* | 4.7* | 749.7 |
| | 22 | 1.95* | 5.1* | 1076 |
| | 25 | 2.02* | 5.7* | 1043 |
| | 29 | 2.32* | 6.6* | 1085 |
| | 48 | 4.71 | 11.9 | 1106 |
| | 77 | 6.31 | 14.9 | 505.7 |

*Value substantially outside of the normal range for this parameter in the cynomolgus monkey based on the Testing Facility's historical database The RBC and hemoglobin levels in Animal 1037 remained significantly reduced and reticulocytes remained significantly elevated (compared to prestudy) up to Day 29. However, by Day 48, the RBC, hemoglobin, and reticulocytes began to recover, and by Day 77, these parameters returned to prestudy levels. Additionally, the changes in these hematology parameters observed in Animal 1036 began to recover on Day 22, and returned to prestudy levels by Day 77. Thus, while Animal 1037 appeared to be more sensitive to the anemia associated with the administration of Hu5F9-G4, termination of dosing (on Day 15) shows that over time, the anemia is reversible. Changes in RBC morphology were also observed in both animals, and consistent with the previous studies, included minimal to marked anisocytosis, microcytes, polychromasia, and spherocytes.

Toxicokinetics showed that serum Hu5F9-G4 concentrations were similar between the two animals from Day 1 through 4 hours post-dose on Day 15 (the dose holiday for Animal 1037 began on Day 15). The $T_{1/2}$ for both monkeys ranged from 173 to 212 hours.

In summary, the treatment related effects in this study was consistent with the previous studies, and included changes in hematology and clinical chemistry parameters. All of these treatment-related changes, including the severe anemia observed in Animal 1037, were reversible, and returned to normal ranges by the end of the study. In addition, despite the anemia observed, no clinical signs of toxicity were observed in either animal.

8-Week Toxicity Study of Hu5F9-G4 by Intravenous Infusion in Cynomolgus Monkeys with an 8-Week Recovery Period The purpose of this GLP study was to evaluate the potential toxicity and toxicokinetics of Hu5F9-G4 when administered to cynomolgus monkeys as a priming dose followed by repeat maintenance doses. Due to the severe anemia with the priming/maintenance dose of 5/150 mg/kg observed in Animal No. 1037 in the previous study, the priming and highest maintenance dose used in this study was 5/100 mg/kg to provide a reasonable safety margin for the doses proposed in the clinical study. Vehicle or Hu5F9-G4 (5 mg/kg) was administered via a 1-hour IV infusion as a priming dose at 5 mg/kg on Day 1 followed by maintenance doses of vehicle or Hu5F9-G4 at doses of 5, 10, 50, or 100 mg/kg administered twice weekly for 7 consecutive weeks (Days 8, 11, 15, 18, 22, 25, 29, 32, 36, 39, 43, 46, 50, and 53). The same dose level (5 mg/kg) was employed for the priming and maintenance doses for Group 5. Recovery animals were included in the vehicle and high dose groups to assess the reversibility of any treatment-related effect. The study design is presented in Table 14.

TABLE 14

8-Week Toxicology Study in Cynomolgus Monkeys

| | Dose[A] (mg/kg) | | No. Males/ | |
|---|---|---|---|---|
| Group | Priming | Maintenance | Females | No. Males/Females |
| 1 | 0 (vehicle) | 0 (vehicle) | 3/3 | 2/2 |
| 2 | 5 | 10 | 3/3 | — |
| 3 | 5 | 50 | 3/3 | 2/2 |
| 4 | 5 | 100 | 3/3 | 2/2 |
| 5 | 5 | 5 | 2/2 | |

[A]The priming dose was administered on Day 1, and the maintenance dose was administered twice weekly on Days 8, 11, 15, 18, 22, 25, 29, 32, 36, 39, 43, 46, 50, and 53.

Safety pharmacology parameters were incorporated into this study and included assessment of respiratory function (visual respiratory rate, cardiovascular function (ECGs), and changes in clinical signs (e.g., activity, behavior) indicative of an effect on central nervous system function. Blood samples were collected throughout the study for toxicokinetics and assessment of ADA responses, as well as to evaluate receptor occupancy of CD47. Throughout the duration of the study, clinical pathology samples were evaluated to assess specific parameters (e.g., hemoglobin, RBC, reticulocytes) based on data from previous studies. Severe anemia was observed in two animals (Animal No. 3002; Group 3, priming/maintenance dose 5/50 mg/kg; Animal No. 4504; Group 4, priming/maintenance dose 5/100 mg/kg), and these animals were placed on dose holidays to evaluate the recovery of the anemia and how the animals responded once dosing resumed. Animal No. 3002 had dose holidays for maintenance doses 6-9 (Days 25, 29, 32, and 36), and dosing resumed on Day 39 (maintenance dose 10). Animal No. 4504 was place on dose holiday on Day 25 (dose 6), and continued on dose holiday until the end of the dose period. Main study animals were terminated on Day 57 and recovery animals were terminated on Day 109. The in-life portion of the study is complete, and all data for main study animals, including histopathology, is available. Data from recovery animals will be submitted when available.

No unscheduled deaths occurred in this study, and administration of Hu5F9-G4 was clinically well-tolerated. No treatment-related effects were observed in clinical signs, body weights, physical and ophthalmology examinations, body temperature, ECGs, respiration or heart rate, coagulation or urinalysis parameters, organ weights, or macroscopic and microscopic examinations.

Consistent with the previous pilot studies, treatment-related changes were observed in all Hu5F9-G4-treated groups in hematology parameters and included mild to moderate decreases in red cell mass (including RBC count, hemoglobin, and hematocrit), which were most pronounced following the priming dose on Day 1; these changes in hematology parameters showed a continued trend to recover by the end of the dosing phase (see Table 15 for changes in hemoglobin levels). While the decrease in RBC count, hemoglobin, and hematocrit were observed in all Hu5F9-G4-treated groups, these changes did not occur in a clear dose-dependent manner. Increases in reticulocytes were observed in all Hu5F9-G4-treated groups, indicative of a robust erythropoietic response associated with the decreases in RBC mass. Consistent with the previous studies, the decreased red cell mass was associated with decreases in MCV and haptoglobin, and increases in MCHC, reticulocytes, and RDW. Free plasma hemoglobin was not observed in any dose groups. Minimal to mild increases in lymphocytes were also observed, but these increases were transient and sporadic in nature and did not occur in a dose-dependent manner. A minimal to mild increase in platelets was observed on Day 8 (which was statistically significant compared to control for most groups), but began to return to control values in most groups by Day 11. This increase in platelets was considered to be a reactive thrombopoiesis and physiological response to the accelerated erythropoiesis, which was evident by concomitant increases in reticulocytes. All of these treatment-related changes in hematology parameters were partially or completely reversible by the end of the dosing phase.

TABLE 15

Changes in Hemoglobin Levels

| Animal No. | Study Day | HGB (g/dL) |
|---|---|---|
| Group 1 (vehicle control) | | |
| 1001 | Prestudy | 13.3 |
| | 3 | 12.3 |
| | 8 | 13.8 |
| | 11 | 12.0 |
| | 15 | 12.5 |
| | 25 | 12.5 |
| | 39 | 13.2 |
| | 57 | 12.4 |
| 1002 | Prestudy | 13.8 |
| | 3 | 12.8 |
| | 8 | 13.6 |
| | 11 | 12.5 |
| | 15 | 12.9 |
| | 25 | 12.6 |
| | 39 | 13.1 |
| | 57 | 12.6 |
| 1003 | Prestudy | 13.8 |
| | 3 | 13.1 |
| | 8 | 13.5 |
| | 11 | 12.7 |
| | 15 | 13.0 |
| | 25 | 13.4 |
| | 39 | 13.2 |
| | 57 | 13.0 |
| 1104 | Prestudy | 14.6 |
| | 3 | 14.8 |
| | 8 | 14.9 |
| | 11 | 13.7 |
| | 15 | 13.8 |
| | 25 | 14.1 |
| | 39 | 13.8 |
| | 57 | 12.4 |
| | 74 | 13.8 |
| | 109 | 14.7 |
| 1005 | Prestudy | 14.8 |
| | 3 | 13.0 |
| | 8 | 13.9 |
| | 11 | 11.9 |
| | 15 | 12.4 |
| | 25 | 13.0 |
| | 39 | 13.1 |
| | 57 | 12.0 |
| | 74 | 12.6 |
| | 109 | 13.6 |
| 1501 | Prestudy | 12.9 |
| | 3 | 11.7 |
| | 8 | 12.3 |

TABLE 15-continued

Changes in Hemoglobin Levels

| Animal No. | Study Day | HGB (g/dL) |
|---|---|---|
| | 11 | 11.4 |
| | 15 | 11.6 |
| | 25 | 11.9 |
| | 39 | 11.9 |
| | 57 | 11.5 |
| 1502 | Prestudy | 13.0 |
| | 3 | 11.9 |
| | 8 | 12.5 |
| | 11 | 11.7 |
| | 15 | 11.8 |
| | 25 | 12.4 |
| | 39 | 12.2 |
| | 57 | 13.4 |
| 1603 | Prestudy | 13.7 |
| | 3 | 12.3 |
| | 8 | 12.7 |
| | 11 | 11.2 |
| | 15 | 12.4 |
| | 25 | 12.3 |
| | 39 | 11.5 |
| | 57 | 10.6 |
| 1504 | Prestudy | 15.1 |
| | 3 | 13.5 |
| | 8 | 13.8 |
| | 11 | 13.0 |
| | 15 | 12.9 |
| | 25 | 12.6 |
| | 39 | 13.1 |
| | 57 | 12.7 |
| | 74 | 13.1 |
| | 109 | 13.8 |
| 1505 | Prestudy | 13.6 |
| | 3 | 12.5 |
| | 8 | 13.3 |
| | 11 | 13.1 |
| | 15 | 12.6 |
| | 25 | 12.8 |
| | 39 | 12.9 |
| | 57 | 9.9 |
| | 74 | 12.6 |
| | 109 | 13.1 |
| Group 2 (5/10 mg/kg) | | |
| 2001 | Prestudy | 14.1 |
| | 3 | 12.6 |
| | 8 | 12.5 |
| | 11 | 11.4 |
| | 15 | 12.4 |
| | 25 | 12.6 |
| | 39 | 12.7 |
| | 57 | 12.0 |
| 2002 | Prestudy | 15.9 |
| | 3 | 12.1 |
| | 8 | 11.8 |
| | 11 | 10.8 |
| | 15 | 11.6 |
| | 25 | 13.5 |
| | 39 | 13.8 |
| | 57 | 12.6 |
| 2003 | Prestudy | 14.1 |
| | 3 | 11.5 |
| | 8 | 11.2 |
| | 11 | 9.8 |
| | 15 | 10.1 |
| | 25 | 11.9 |
| | 39 | 12.7 |
| | 57 | 11.6 |
| 2501 | Prestudy | 13.7 |
| | 3 | 11.3 |
| | 8 | 10.7 |
| | 11 | 8.8 |
| | 15 | 8.9 |
| | 25 | 11.4 |
| | 39 | 13.0 |
| | 57 | 11.7 |

TABLE 15-continued

Changes in Hemoglobin Levels

| Animal No. | Study Day | HGB (g/dL) |
|---|---|---|
| 2502 | Prestudy | 13.0 |
| | 3 | 10.4 |
| | 8 | 10.2 |
| | 11 | 9.1 |
| | 15 | 10.1 |
| | 25 | 10.5 |
| | 39 | 11.4 |
| | 57 | 9.9 |
| 2503 | Prestudy | 14.3 |
| | 3 | 12.0 |
| | 8 | 12.1 |
| | 11 | 9.9 |
| | 15 | 10.0 |
| | 25 | 11.5 |
| | 39 | 13.0 |
| | 57 | 12.1 |
| Group 3 (5/50 mg/kg) | | |
| 3001 | Prestudy | 14.9 |
| | 3 | 12.8 |
| | 8 | 12.1 |
| | 11 | 11.2 |
| | 15 | 11.7 |
| | 25 | 13.2 |
| | 39 | 14.1 |
| | 57 | 13.2 |
| 3003 | Prestudy | 13.9 |
| | 3 | 10.8 |
| | 8 | 11.3 |
| | 11 | 10.1 |
| | 15 | 10.0 |
| | 25 | 12.4 |
| | 39 | 13.4 |
| | 57 | 12.0 |
| 3104 | Prestudy | 14.6 |
| | 3 | 13.0 |
| | 8 | 13.7 |
| | 11 | 12.3 |
| | 15 | 11.8 |
| | 25 | 12.7 |
| | 39 | 13.4 |
| | 57 | 12.3 |
| | 74 | 13.0 |
| | 109 | 13.8 |
| 3005 | Prestudy | 14.6 |
| | 3 | 12.1 |
| | 8 | 13.0 |
| | 11 | 11.9 |
| | 15 | 12.1 |
| | 25 | 13.3 |
| | 39 | 13.6 |
| | 57 | 12.5 |
| | 74 | 13.1 |
| | 109 | 12.5 |
| 3601 | Prestudy | 15.0 |
| | 3 | 11.4 |
| | 8 | 12.0 |
| | 11 | 10.2 |
| | 15 | 10.9 |
| | 25 | 11.6 |
| | 39 | 11.8 |
| | 57 | 10.4 |
| | 74 | 12.0 |
| | 109 | 14.1 |
| 3602 | Prestudy | 13.2 |
| | 3 | 10.9 |
| | 8 | 10.3 |
| | 11 | 8.7 |
| | 15 | 8.8 |
| | 25 | 11.2 |
| | 39 | 12.2 |
| | 50 | 8.1 |
| | 57 | 7.0 |
| | 67 | 8.8 |
| | 74 | 10.9 |
| | 109 | 13.4 |
| 3503 | Prestudy | 13.0 |
| | 3 | 10.4 |
| | 8 | 10.1 |
| | 11 | 9.0 |
| | 15 | 8.5 |
| | 25 | 10.2 |
| | 39 | 11.0 |
| | 57 | 10.1 |
| 3504 | Prestudy | 12.8 |
| | 3 | 10.9 |
| | 8 | 11.9 |
| | 11 | 10.5 |
| | 15 | 10.6 |
| | 25 | 10.7 |
| | 39 | 10.8 |
| | 57 | 11.0 |
| 3505 | Prestudy | 13.4 |
| | 3 | 11.0 |
| | 8 | 11.1 |
| | 11 | 10.2 |
| | 15 | 10.8 |
| | 25 | 11.1 |
| | 39 | 12.0 |
| | 57 | 11.4 |
| Group 4 (5/100 mg/kg) | | |
| 4001 | Prestudy | 13.5 |
| | 3 | 10.5 |
| | 8 | 9.8 |
| | 11 | 8.9 |
| | 15 | 9.3 |
| | 25 | 10.0 |
| | 39 | 12.1 |
| | 57 | 11.5 |
| 4102 | Prestudy | 13.5 |
| | 3 | 10.7 |
| | 8 | 9.5 |
| | 11 | 9.2 |
| | 15 | 10.0 |
| | 25 | 11.4 |
| | 39 | 11.3 |
| | 57 | 11.4 |
| 4103 | Prestudy | 14.8 |
| | 3 | 11.3 |
| | 8 | 10.4 |
| | 11 | 9.5 |
| | 15 | 10.2 |
| | 25 | 12.0 |
| | 39 | 13.5 |
| | 57 | 12.4 |
| 4004 | Prestudy | 13.8 |
| | 3 | 10.9 |
| | 8 | 10.0 |
| | 11 | 9.1 |
| | 15 | 9.8 |
| | 25 | 12.4 |
| | 39 | 12.8 |
| | 57 | 11.9 |
| | 74 | 12.4 |
| | 109 | 12.5 |
| 4005 | Prestudy | 14.2 |
| | 3 | 11.6 |
| | 8 | 11.4 |
| | 11 | 9.6 |
| | 15 | 8.8 |
| | 25 | 11.1 |
| | 39 | 12.4 |
| | 57 | 11.1 |
| | 74 | 12.2 |
| | 109 | 12.7 |
| 4501 | Prestudy | 13.0 |
| | 3 | 9.7 |
| | 8 | 10.4 |

TABLE 15-continued

Changes in Hemoglobin Levels

| Animal No. | Study Day | HGB (g/dL) |
|---|---|---|
| | 11 | 8.4 |
| | 15 | 8.4 |
| | 25 | 8.8 |
| | 39 | 10.4 |
| | 57 | 10.4 |
| 4502 | Prestudy | 13.5 |
| | 3 | 11.7 |
| | 8 | 11.8 |
| | 11 | 9.7 |
| | 15 | 11.0 |
| | 25 | 11.9 |
| | 39 | 12.9 |
| | 57 | 12.3 |
| 4503 | Prestudy | 13.6 |
| | 3 | 11.4 |
| | 8 | 12.1 |
| | 11 | 11.0 |
| | 15 | 10.6 |
| | 25 | 13.0 |
| | 39 | 13.5 |
| | 57 | 13.2 |
| 4505 | Prestudy | 13.3 |
| | 3 | 11.5 |
| | 8 | 11.3 |
| | 11 | 9.8 |
| | 15 | 9.1 |
| | 25 | 10.2 |
| | 39 | 11.2 |
| | 57 | 11.0 |
| Group 5 (5/5 mg/kg) | | |
| 5001 | Prestudy | 14.4 |
| | 3 | 12.2 |
| | 8 | 11.9 |
| | 11 | 11.7 |
| | 15 | 12.4 |
| | 25 | 13.1 |
| | 39 | 14.5 |
| | 57 | 13.3 |
| 5002 | Prestudy | 14.3 |
| | 3 | 12.4 |
| | 8 | 11.9 |
| | 11 | 11.5 |
| | 15 | 11.7 |
| | 25 | 12.2 |
| | 39 | 12.8 |
| | 57 | 12.8 |
| 5501 | Prestudy | 13.9 |
| | 3 | 10.7 |
| | 8 | 10.7 |
| | 11 | 9.8 |
| | 15 | 10.1 |
| | 25 | 11.7 |
| | 39 | 13.6 |
| | 57 | 12.0 |
| 5502 | Prestudy | 14.0 |
| | 3 | 11.4 |
| | 8 | 10.9 |
| | 11 | 10.6 |
| | 15 | 10.9 |
| | 25 | 12.4 |
| | 39 | 12.9 |
| | 57 | 12.0 |

While the hemoglobin decreased in all Hu5F9-G4-treated animals following the administration of the priming dose on Day 1, the decrease in hemoglobin was generally most pronounced following administration of the first maintenance dose on Day 8 (see Day 11 hemoglobin levels in Table 16). The extent of the decrease in hemoglobin was varied across animals, and the incidence of animals having a hemoglobin level ≤10.0 g/dL on Day 11 was 67%, 30%, 90%, and 50% for Groups 2 (2/10 mg/kg), 3 (5/50 mg/kg), 4 (5/100 mg/kg) and 5 (5/5 mg/kg), respectively. While the anemia (on Day 11) did not occur in a clear dose-dependent manner between Groups 2, 3, or 5, Group 4 had the highest number of animals that had a hemoglobin level ≤10.0 g/dL. Overall, a continued trend in recovery in hemoglobin was observed across animals, starting around Days 15 to 32 and continuing until the end of the study. One exception, however, was noted near the end of the study where Animal No. 3602 had another substantial reduction in hemoglobin following administration of the $11^{th}$ maintenance dose Day 46 (hemoglobin decreased as low as 7.0 g/dL on Days 55 and 57; Table 16). The hemoglobin level for Animal No. 3602, however, began to recover on Day 60 (7 days after the last maintenance dose), and returned to prestudy levels (13.4 g/dL) by the end of the study on Day 109. Due to the severe anemia observed, two animals (Animal No. 3002; Group 3, priming/maintenance dose 5/50 mg/kg; Animal No. 4504; Group 4, priming/maintenance dose 5/100 mg/kg) were placed on dosing holidays to evaluate the recovery of the anemia and how the animals respond once dosing resumed. Animal No. 3002 showed more severe anemia (as low as 5.7 g/dL on Days 15 and 18) and had dose holidays for maintenance doses 6-9 (Days 25, 29, 32, and 36); dosing resumed on Day 39 (maintenance dose 10). Animal No. 4504 was place on dose holiday on Day 25 (dose 6), and continued on dose holiday until the end of the dose period (see Table 16 to see changes in hemoglobin levels). The changes in RBC count, hemoglobin, and reticulocytes noted in Animal No. 3002 began to recover on Day 36, and continued to recover to the end of the study on Day 57. Likewise, the hematology changes in Animal No. 4504 started to recover, and showed a continued trend to recovery until the end of the study (Day 109; this animal was in the recovery group). Thus, while it appears that a low number of animals may be especially sensitive to the anemia produced by Hu5F9-G4, the anemia is transient and the hemoglobin levels recover over time.

TABLE 16

Hematology Parameters for Animals Placed on Dose Holiday

| Group/Animal No. | Study Day | HGB (g/dL) |
|---|---|---|
| 3/3002[A] | Pre-study | 14.4 |
| | 3 | 10.8 |
| | 8 | 9.6 |
| | 11 | 6.9 |
| | 15 | *5.7 |
| | 18 | *5.7 |
| | 25 | *5.9 |
| | 36 | 12.2 |
| | 46 | 10.3 |
| | 57 | 11.0 |
| 4/4504[B] | Pre-study | 13.7 |
| | 3 | 11.2 |
| | 8 | 11.7 |
| | 11 | 9.6 |
| | 15 | 7.3 |
| | 18 | *6.9 |
| | 25 | 7.1 |
| | 36 | 7.2 |
| | 46 | 8.4 |
| | 57 | 11.0 |
| | 74 | 12.9 |
| | 109 | 13.0 |

[A]Animal No. 3002 was placed on dose holiday on Day 25 and dosing resumed on Day 39; main study animal and terminated on Day 57
[B]Animal 4504 was placed on dose holiday on Day 25 and remained on dose holiday to the end of the study; recovery animal and terminated on Day 109
*Significantly below the normal range for cynomolgus monkeys based on Testing Facility's historical database Changes in blood cell morphology were consistent with previous studies and considered to be associated with accelerated red blood cell destruction/clearance and increased erythropoiesis. These changes ranged from minimal to marked in nature and included anisocytosis, spherocytes (microcytes), polychromasia, as well as eccentrocytes and atypical erythrocyte fragments consistent with erythrocyte injury/clearance. The variability in the range of red blood cell size was due to the mixture of smaller spherocytes and larger polychromatophils (reticulocytes). A transient increase was also observed in the number of nucleated erythrocytes in the circulation of several Hu5F9-G4-treated animals. Changes in red blood cell morphology showed continued trends of recovery to the end of the study. Changes in bone marrow smear evaluations were minimal to moderate and limited to morphologic changes in the erythroid lineage (dysplasia), which consisted of occasional cells with abnormal nuclear shapes, multiple nuclei, nuclear blebbing, and/or nuclear to cytoplasm maturation asynchrony (abnormal nucleus to cytoplasm maturation). Additional changes were considered to be related to the accelerated erythropoietic response associated with Hu5F9-G4 which included mild decreases in the mean M:E ratio in Group 3 and Group 4 (females only) animals along with an appropriate minimal to mild shift to more immature erythroid precursors associated with accelerated erythropoiesis.

Consistent with previous studies, treatment related changes in hematology parameters (i.e., decreased RBC and hemoglobin; increased reticulocytes) were associated with increases in total bilirubin and decreases in haptoglobin. Other changes in clinical chemistry parameters were observed only in the high dose group (5/100 mg/kg) and included a slight decrease in albumin (two female animals), a slight increase in globulin, and a corresponding decrease in albumin:globulin ratio. All treatment-related changes in clinical chemistry parameters were partially or completely reversible at the end of the dosing phase.

The Day 8 toxicokinetics showed that following a priming dose of 5 mg/kg on Day 1, and an initial maintenance dose at 5, 10, 50 or 100 mg/kg on Day 8, increases in $C_{max}$ were dose proportional from 10 to 100 mg/kg, but greater than dose proportional from 5 to 100 mg/kg. While increases in $AUC_{0-72}$ trended towards dose proportional between 50 and 100 mg/kg, changes in $AUC_{0-72}$ were greater than dose proportional from 5 to 100 or 10 to 100 mg/kg. The mean $T_{1/2}$ appeared to increase with increasing dose and ranged from 6 hours at 5 mg/kg to 52 hours at 100 mg/kg. There were no obvious gender differences in exposure. Day 25 toxicokinetics showed that following twice weekly dosing at 5, 10, 50 or 100 mg/kg for 3 weeks, increases in exposure ($C_{max}$, $AUC_{0-72}$) were greater than dose proportional from 5 to 100 mg/kg but dose proportional from 10 to 100 mg/kg. In addition, exposure trended lower in female compared to male monkeys. The apparent $T_{1/2}$ was shorter at 5 mg/kg relative to the higher doses. In some animals, $T_{1/2}$ was similar between Day 25 and Day 8, and in other animals, $T_{1/2}$ appeared to be longer on Day 25; the mean $T_{1/2}$ ranged from 6.3 hours (5 mg/kg) to 66 hours (50 mg/kg). Day 53 toxicokinetics following twice weekly dosing at 5, 10, 50 or 100 mg/kg for 7 weeks, showed increases in exposure ($C_{max}$) $AUC_{0-72}$) were greater than dose proportional from 5 to 100 mg/kg but dose proportional from 10 to 100 mg/kg.

Concentration vs. time profiles on Day 53 relative to Day 25 or Day 8 suggested that circulating concentrations of Hu5F9-G4 continued to increase with repeat dosing. With the exception of the 5 mg/kg dose (which appeared to be impacted by ADA), mean and median exposure ($C_{max}$, $AUC_{0-72}$) on Day 53, within each dose group, were generally higher than that on Day 25 or Day 8, suggesting further accumulation of Hu5F9-G4 with continued twice weekly dosing. While the development of ADA appears to impact exposure, this impact was primarily noted at the 5 mg/kg maintenance dose, and overall, exposure was maintained throughout the study at doses 10 mg/kg maintenance doses.

In summary, treatment-related findings were consistent with previous studies, and included changes in hematology and clinical chemistry parameters and bone marrow cytology. Changes in hematology parameters included decreases in RBC count and hemoglobin combined with reticulocytosis. Importantly, free plasma hemoglobin was not detected in any animal throughout the study. While the anemia related to Hu5F9-G4 did not occur in a clear dose-dependent manner between Groups 2, 3, or 5, the number of animals having a hemoglobin level ≤10.0 g/dL was greatest in Group 5, which was administered the highest maintenance dose (100 mg/kg). While the hemoglobin levels generally showed a trend in recovery across all animals starting around Days 15-32 and continued to the end of the study, a substantial decrease in hemoglobin was noted again in one animal (Group 3) near the end of the study following the administration of the 11$^{th}$ maintenance dose on Day 46. The hemoglobin for this animal, however, returned to prestudy levels by the end of the study (Day 109). Two animals (one each in Groups 3 and 4) were placed on dose holiday due to the severe anemia observed in each animal. Importantly, despite the severe anemia observed in these animals, no clinical signs of toxicity were noted and the hemoglobin level in each animal showed a continued trend to recovery until the study end. Changes in red blood cell morphology were consistent with accelerated red blood cell destruction/clearance and increased erythropoiesis and consisted of atypical erythrocyte fragments, anisocytosis, spherocytes (microcytes), and polychromasia. Changes in hematology parameters were associated with increased total bilirubin and decreased haptoglobin. Other treatment-related changes in clinical chemistry parameters were noted only in the high dose group and included a slight decrease in albumin, slight increase in globulin, and the corresponding albumin:globulin (A:G) ratio. All of these treatment-related changes were either partially or completely reversible in all Hu5F9-G4-treated groups by the end of the study. Changes in bone marrow cytology were limited to morphologic changes in the erythroid lineage consisting of occasional cells with abnormal nuclear shapes, multiple nuclei, nuclear blebbing, and/or nuclear to cytoplasm maturation asynchrony.

Overall, administration of Hu5F9-G4 via a 1-hour IV infusion as a priming dose of 5 mg/kg in Week 1 (Day 1), followed by twice weekly maintenance doses for 7 consecutive weeks at doses up to 100 mg/kg was clinically well-tolerated in cynomolgus monkeys. Despite the treatment-related anemia, including the animals having dose holidays, no signs of clinical toxicity were observed. The changes observed in this study were consistent with previous studies, and considered to be related to the pharmacological action of Hu5F9-G4 in accelerating the process of aging RBC elimination through binding to CD47 expressed on RBCs. Therefore, based on the totality of the data, the highest-non-severely-toxic-dose (HNSTD) for this study was considered to be the priming/maintenance dose of 5/100 mg/kg, the highest dose evaluated.

Genotoxicity

The range and type of genotoxicity studies routinely conducted for small molecule drug products are generally not applicable to biotechnology-derived products [ICH S6(R1)]. It is not expected that a monoclonal antibody, such as Hu5F9-G4, would interact directly with DNA or other chromosomal material. Thus, mutagenicity studies are considered inappropriate and are not planned.

Carcinogenicity

No carcinogenicity studies have been conducted with Hu5F9-G4. Based on the mechanism of action of Hu5F9-G4, it is not expected to be carcinogenic. Additionally, Hu5F9-G4 is neither a growth factor nor immunosuppressant. Thus, given the intended patient population and lack of mechanistic concern, carcinogenicity studies are not planned.

Reproductive and Developmental Toxicity

Reproductive and developmental toxicity studies have not been performed with Hu5F9-G4. While a formal, stand-alone fertility study will not be performed; no treatment-related effects were noted in the microscopic examination of male and female reproductive organs in the 8-week toxicity study. Since the potential teratogenic effects of Hu5F9-G4, if any, in laboratory animals is unknown, Hu5F9-G4 should not be administered to pregnant women. To avoid pregnancy, appropriate precautions will be taken for male and female patients of child bearing potential enrolled in the proposed Phase 1 clinical study (e.g., women must demonstrate a negative pregnancy test, patients must consent to adequate contraceptive precautions, etc.).

Local Tolerance

No stand-alone local tolerance studies have been performed; however, consistent with ICH S6(R1), evaluation of local tolerance of Hu5F9-G4 (clinical observations, macro- and microscopic examination of tissue samples from the injection site) were performed as part of the repeat dose toxicity studies.

Discussion and Conclusions

A comprehensive series of toxicology studies was conducted in support of administration of Hu5F9-G4 in the proposed clinical trial. These studies included an in vitro hemolysis study, single- and multiple-dose studies in rhesus and cynomolgus monkeys, and a tissue cross reactivity study in a panel of human tissues.

The major and consistent treatment related finding across all of the monkey studies was anemia (as reflected in decreased RBC count and hemoglobin). The anemia generally developed following administration of the first dose (or priming dose in the priming/maintenance dose schedule studies), and was associated with changes indicative of the accelerated clearance of RBCs and responsive erythropoiesis, including reticulocytosis, and alterations in RBC morphologies such as anisocytosis, polychromasia, and spherocytosis. Importantly, free plasma hemoglobin was not observed across all of the studies. The changes in hematology parameters associated with Hu5F9-G4 were generally associated with changes in haptoglobin and total bilirubin; Haptoglobin was often, but not always reduced, and increases in total bilirubin were generally observed; changes in haptoglobin and total bilirubin, however, did not occur in a dose-dependent manner. Across all studies, changes in hematology and clinical chemistry parameters associated with Hu5F9-G4 showed trends of recovery during the study, and were either partially or completely reversible by the end of the study. Changes in bone marrow cytology (performed in the GLP 8-week study; PR013) were considered to be associated with accelerated erythropoiesis and included morphologic changes in the erythroid lineage, decreases in the mean M:E ratio, and an appropriate shift to more immature erythroid precursors associated with accelerated erythropoiesis.

Based on the known role of CD47 in the normal clearance of aging red blood cells and the combined data obtained across the monkey studies, the primary treatment-related changes (i.e., anemia) are considered to be related to the pharmacological action of Hu5F9-G4 binding to CD47 expressed on RBCs. We believe that the administration of Hu5F9-G4 accelerates the process of elimination of aging RBCs by substituting gradual loss of CD47 with immediate blockade of CD47 on aging RBCs. The premature loss of aging RBCs is compensated by an ensuing reticulocytosis (which was observed across all studies), and over time, the initial anemia resolves as the aged RBCs are replaced with younger cells, and as a result, the age distribution of the RBC pool is shifted to younger cells.

Despite the anemia related to administration of Hu5F9-G4, no evidence of toxicity was observed in clinical signs in any animal, and thus, Hu5F9-G4 was clinically well-tolerated, even at doses as high as 300 mg/kg. While administration of Hu5F9-G4 resulted in a transient anemia, no clinical signs of toxicity were noted, and Hu5F9-G4 was clinically well-tolerated by monkeys, even a doses as high as 300 mg/kg. The toxicology studies, however, did reveal that a small number of animals are particularly sensitive to the Hu5F9-G4-associated anemia. While it is unknown at this time why these monkeys are more sensitive to the anemia produced by Hu5F9-G4, the anemia is transient, and consistently showed a trend to recover upon termination of dosing. Since certain patients may be more sensitive than others, changes in hematology will be rigorously monitored in the proposed clinical study, and appropriate measures will be taken for any patient developing anemia below pre-specified levels.

The anemia related to Hu5F9-G4 was partially or completely reversible across all of the monkey studies, and resolved for animals that were placed on dose holiday, including those animals where dosing had resumed. The HNSTD for the 8-week toxicology study was the priming/maintenance dose of 5/100 mg/kg (the highest dose tested). Based on toxicokinetics data, the 5 mg/kg priming dose used in the 8-week toxicology study is predicted to provide a safety margin (AUC-based) ranging from 28- to 194-fold above the proposed starting priming dose of 0.1 mg/kg in the planned clinical trial. The twice weekly maintenance dose of 100 mg/kg provides a predicted safety margin (based on AUC) ranging from 766-803-fold above the starting maintenance dose of 0.1 mg/kg planned for the proposed clinical study.

In summary, based on the results from the toxicology studies, the nonclinical safety assessment program supports the administration of Hu5F9-G4 (e.g., as an IV infusion) for the proposed clinical trial.

What is claimed is:

1. A method of treating a mammalian subject with cancer with a therapeutic dose of an anti-CD47 agent that blocks the interaction between CD47 and SIRPα, selected from: an antibody that binds to CD47; an antibody that binds to SIRPα; a soluble SIRPα-binding CD47 fragment; and a soluble CD47-binding SIRPα fragment or a combination thereof, for treatment of the cancer, the method comprising:

(a) administering a sub-therapeutic dose of one of the anti-CD47 agents to the subject, wherein the sub-therapeutic dose is effective to increase production of reticulocytes; and (b) administering a therapeutically effective dose of at least one of the anti-CD47 agents to the subject, wherein step (b) is performed in a range from about 3 days to about 21 days after beginning step (a).

2. The method according to claim 1, wherein step (b) is performed in a range from about 6 days to about 8 days after beginning step (a).

3. The method according to claim 1, further comprising after step (a) and prior to step (b): a step of determining whether administration of the sub-therapeutic dose was effective by detecting in a blood sample from the subject one or more of: an increase in the absolute or relative number of reticulocytes; an increase in the level of EPO; or a decrease in hemoglobin levels.

4. The method according to claim 3, wherein the determining step comprises performing a reticulocyte count, wherein administration of the sub-therapeutic dose is determined to have been effective if the reticulocyte count is about $400 \times 10^9$ reticulocytes per liter (L) or more.

5. The method according to claim 3, wherein the determining step is performed in a range from about 3 days to about 12 days after beginning step (a).

6. The method according to claim 1, further comprising after step (a) and prior to step (b):

administering a second sub-therapeutic dose of one of the anti-CD47 agents to the subject wherein step (b) is performed in a range from about 3 days to about 21 days after administering the second sub-therapeutic dose.

7. The method according to claim 1, wherein step (b) comprises administering the anti-CD47 agent in two or more doses of escalating concentration until a therapeutically effective dose is administered.

8. The method according to claim 1, wherein step (b) comprises administering two or more therapeutically effective doses.

9. The method according to claim 1, comprising administering in the therapeutic dose of (b) a combination of two or more anti-CD47 agents to the subject.

10. The method of claim 1, wherein the mammalian subject is a human.

11. A method of treating a human subject with cancer with a therapeutic dose of an anti-CD47 antibody that blocks the interaction between CD47 and SIRPα for treatment of the cancer, the method comprising:

(a) administering a sub-therapeutic dose of the anti-CD47 antibody to the subject wherein the sub-therapeutic dose is sufficient to increase production of reticulocytes; and (b) administering a therapeutically effective dose of the anti-CD47 antibody to the subject, wherein step (b) is performed in a range from about 3 days to about 21 days after beginning step (a).

12. The method of claim 11, wherein the sub-therapeutic dose is less than 10 mg/kg body weight.

* * * * *